US008673844B2

(12) United States Patent
Ridgway et al.

(10) Patent No.: US 8,673,844 B2
(45) Date of Patent: Mar. 18, 2014

(54) METHOD OF INHIBITING PROGRESSION OF TYPE 1 DIABETES BY ADMINISTERING SOLUBLE CD137

(71) Applicant: University of Cincinnati, Cincinnati, OH (US)

(72) Inventors: William Ridgway, Cincinnati, OH (US); David Erwin Adams, Cincinnati, OH (US); Kritika Kachapati, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 13/655,930

(22) Filed: Oct. 19, 2012

(65) Prior Publication Data

US 2013/0101610 A1 Apr. 25, 2013

Related U.S. Application Data

(60) Provisional application No. 61/548,997, filed on Oct. 19, 2011.

(51) Int. Cl.
*A61K 38/16* (2006.01)

(52) U.S. Cl.
USPC .......................................... 514/1.1; 514/21.2

(58) Field of Classification Search
None
See application file for complete search history.

(56) References Cited

PUBLICATIONS

Melero et al (2008), Trends in Pharmacological Sciences, vol. 29, No. 8, pp. 383-390.*
Kim et al (2010), Endocrinology, 151: 4725-4735.*
Heaney et al (1998), J. Leukoc. Biol., (1998), 64: 135-146.*
Heaney et al (1996), Blood, 87:847-857.*
Liu et al (2006), Scand. J. Immunol. 64(4):412-419.*
Irie, J., et al., "Modulating protective and pathogenic CD4+ subsets via CD137 in Type 1 Diabetes," Diabetes 56 (1):186-96 (2007).
Kachapati, K., et al., "The B10 Idd9.3 locus mediates accumulation of functionally superior CD137+ regulatory T cells in the nonobese diabetic Type 1 diabetes Model," J. Immunol. 189:5001-5015, Oct. 12, 2012.
Kachapati, K., et al., "The non-obese diabetic (NOD) mouse as a model of human Type 1 diabetes," Animal Models of Diabetes Research, Methods Mol. Biol. 933:3-16 (2012).
Langstein, J., et al., CD137 (ILA/4-1BB), a member of the TNF receptor family, induces monocyte activation via bidirectional signaling, J. Immunol. 160(5):2488-94 (1998).
Michel, J., et al., Expression of soluble CD137 correlates with activation-induced cell death of lymphocytes, Cytokine 12(6): 742-46 (2000).
Polte, T., et al., "CD137 ligand prevents the development of T-helper Type 2 cell-mediated allergic asthma by interferon-gamma-producing CD8+ T cells," Clin Exp Allergy, 37(9):1374-85 (2007).
Shao, Z., et al., "Characterisation of soluble murine CD137 and its association with systemic lupus," Molecular Immunology, 45(15): 3990-99 (2008).
Dornmair, K., et al., "T-Cell-Mediated Autoimmunity," Am. J. Pathol. 163(4):1215-26 (2003).
Liu, G.Z., et al., "Decreased 4-1BB expression on CD4+CD25 high regulatory T cells in peripheral blood of patients with multiple sclerosis." Clin Exp Immunol, 154(1):22-9 (2008).
Kwon, B.S., et al., "Genomic organization and chromosomal localization of the T-cell antigen 4-1BB," J. Immunol. 152 (5):2256-62 (1994).

* cited by examiner

*Primary Examiner* — Prema Mertz
(74) *Attorney, Agent, or Firm* — Dinsmore & Shohl LLP

(57) ABSTRACT

A method for treating or preventing a T-cell-mediated autoimmune disease is provided herein, the method including administering to a mammal in need thereof a therapeutically effective amount of soluble CD137 or CD137$^{pos}$ regulatory T cells. Also provided are pharmaceutical compositions for treating or preventing T-cell-mediated autoimmune diseases, the pharmaceutical compositions including a therapeutically effective amount of soluble CD137 or CD137$^{pos}$ regulatory T cells and a pharmaceutically-acceptable carrier.

6 Claims, 18 Drawing Sheets a.

b.

c.

a.

| Lane # | Samples |
|---|---|
| 1 | Bio-Rad prestained SDS-PAGE standards, Low Range |
| 2 | 0.45μg of purified sCD137 HEK293 |
| 3 | Unpurified sCD137 HEK293 |
| 4 | 0.75μg of purified sCD137 HEK293 |
| 5 | 0.2μg of purified CD137-Fc |
| 6 | Bio-Rad prestained SDS-PAGE standards, Low Range |
| 7 | 0.45 μg of purified sCD137 HEK293 + DTT |
| 8 | Unpurified sCD137 HEK293 +DTT |
| 9 | 0.75μg of purified sCD137 HEK293 +DTT |
| 10 | 0.2μg of purified CD137-Fc + DTT |

b.

METHOD OF INHIBITING PROGRESSION OF TYPE 1 DIABETES BY ADMINISTERING SOLUBLE CD137

RELATED APPLICATION

This application claims priority under 35 U.S.C. §119(e) to U.S. Provisional Application Ser. No. 61/548,997, filed Oct. 19, 2011, which is incorporated herein by reference in its entirety.

FIELD OF THE INVENTION

The present invention relates generally to the treatment and prevention of T-cell-mediated autoimmune diseases. Specifically, the present invention relates to methods for treating and preventing T-cell-mediated autoimmune diseases such as type 1 diabetes by administering soluble CD137 or $CD137^{pos}$ regulatory T cells and pharmaceutical compositions comprising the same.

BACKGROUND OF THE INVENTION

Autoimmune diseases affect approximately 5-8% of the population in the United States. Fairweather, D., *Autoimmune Disease: Mechanisms, Encyclopedia of Life Sciences* (2007). Many autoimmune diseases affect young persons and may persist over the lifetime of the individual, leading to a disproportionate burden on public health resources and an annual estimated cost of over 100 billion dollars in the United States.

Autoreactive T cells are key players in autoimmune diseases, acting as both helper and effector cells. Dornmair, K., et al., *T-Cell-Mediated Autoimmunity, Am. J. Pathol.* 163(4): 1215-26 (2003). Studies have shown that the transfer of autoreactive T cells is sufficient to induce autoimmune disease in animal models.

T cells have been shown to mediate a variety of autoimmune diseases, including type 1 diabetes, multiple sclerosis, systemic lupus, psoriasis, and rheumatoid arthritis, and probably play a role, as a part of a coordinated immune response, in many other autoimmune diseases. T regulatory cells suppress immune responses of other cells, including autoreactive T cells, although the molecular mechanisms by which regulatory T cells exert suppressor activity have not been completely characterized. T-cells contribute to most autoimmune diseases, many of which are severely debilitating and may lead to patient death. For example, type 1 diabetes (T1D) remains a major cause of long-term morbidity and mortality in over one percent of population worldwide. Although insulin treatment and islet transplantation are currently the most effective therapeutic regimens, these approaches suffer from limitations and are not always effective to treat the disease. To date, although autoreactive T cells have been proven to mediate T1D, no effective immune-based therapy has reversed T1D. Thus, immune-based therapies modulating autoreactive T cells are desperately needed in T1D. The same holds true for other diseases, such as multiple sclerosis. The need persists for methods and compositions that treat or prevent T-cell-mediated autoimmune disorders.

SUMMARY OF THE INVENTION

It is, therefore, an aspect of the present invention to provide methods and compositions for treating or preventing a T-cell-mediated autoimmune disorder.

In one embodiment, a method of treating or preventing a T-cell-mediated autoimmune disease is provided, the method comprising administering to a mammal in need thereof a therapeutically effective amount of soluble CD137.

In another embodiment, a method of treating or preventing a T-cell-mediated autoimmune disease is provided, the method comprising administering to a mammal in need thereof a therapeutically effective amount of $CD137^{pos}$ regulatory T cells.

In another embodiment, a pharmaceutical composition for the treatment or prevention of a T-cell-mediated autoimmune disease is provided, the pharmaceutical composition comprising: a therapeutically effective amount of soluble CD137; and a pharmaceutically-acceptable carrier.

In another embodiment, a pharmaceutical composition for the treatment or prevention of a T-cell-mediated autoimmune disease is provided, the pharmaceutical composition comprising: a therapeutically effective amount of $CD137^{pos}$ regulatory T cells; and a pharmaceutically-acceptable carrier.

These and other objects, features, embodiments, and advantages will become apparent to those of ordinary skill in the art from a reading of the following detailed description and the appended claims.

DETAILED DESCRIPTION OF THE INVENTION

Figure 1:
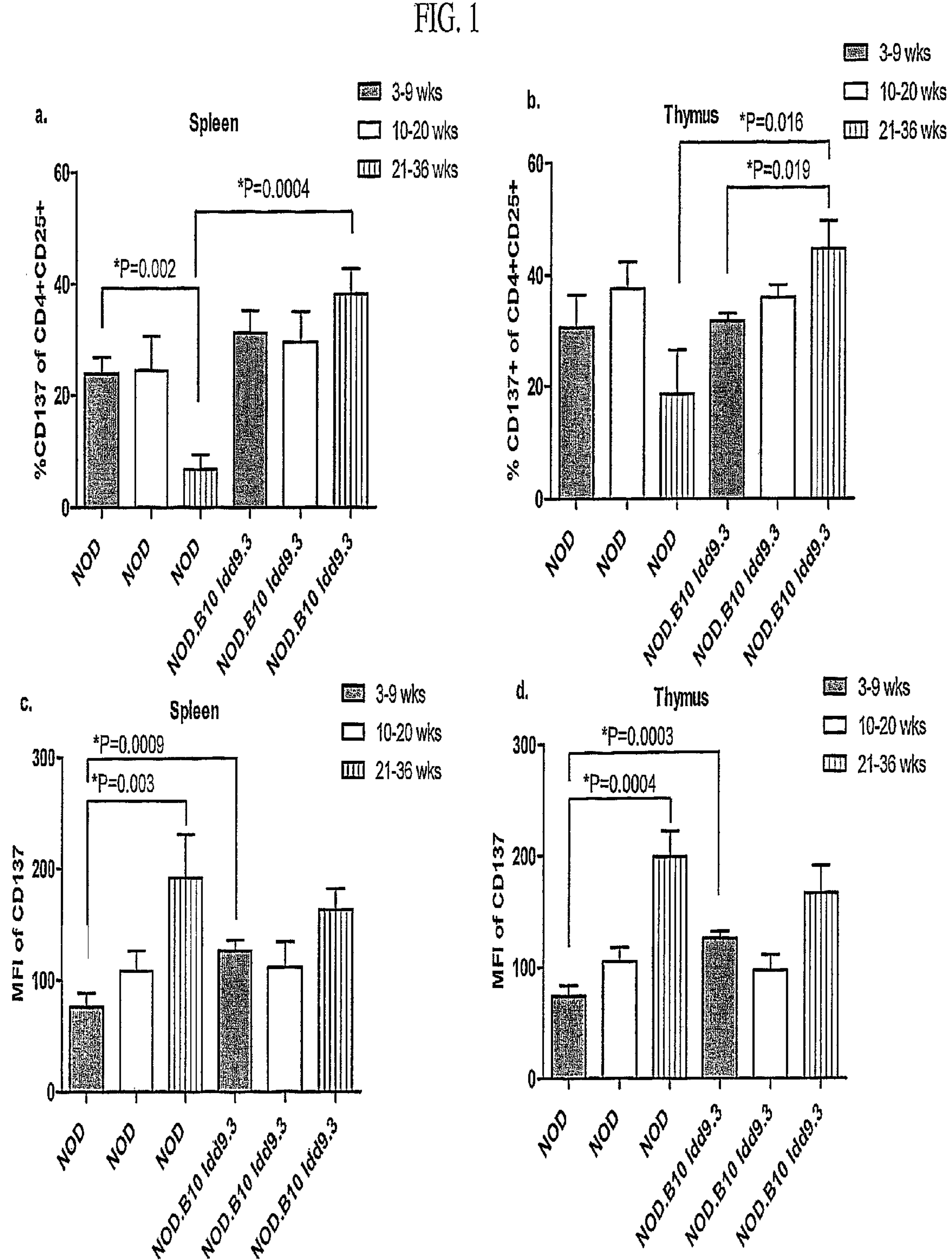
FIG. 1 shows peripheral $CD137^{pos}CD4^{pos}CD25^{pos}$ T cells decline with age in NOD but not NOD.B10 Idd9.3 mice; young NOD.B10 Idd9.3 splenic and thymic Tregs have higher cellular expression of CD137 compared to NOD Tregs. NOD and NOD.B10 Idd9.3 splenocytes (a, c) and NOD and NOD.B10 Idd9.3 thymus thymocytes (b, d) were isolated from 3-36 week old non-diabetic females, stained with CD4-APC, CD25-FITC, and anti-CD137-PE or IgG2a isotype control, and analyzed by flow cytometry. (a, c) NOD spleen included: (n=10) 3-9 wk old, (n=5) 9-20 wk old, and (n=5) 21-36 wk old mice; NOD.B10 Idd9.3 spleen included (n=7) 3-9 wk old, (n=6) 9-20 wk old, and (n=9) 21-36 wk old mice. (b, d) NOD thymus included (n=6) 3-9 wk old, (n=6) 9-20 wk old, and (n=4) 21-36 wk old mice; NOD.B10 Idd9.3 thymus included (n=9) 3-9 wk old, (n=4) 9-20 wk old, and (n=8) 21-36 wk old mice. (a, b) Isotype staining was used to gate for percent CD137 in $CD4^{pos}CD25^{pos}$T cells in NOD and NOD.B10 Idd9.3 spleen and thymus. (c, d) The mean florescence intensity of CD137 on $CD137^{pos}CD4^{pos}CD25^{pos}$ T cells was analyzed on cells from NOD and NOD.B10 Idd9.3 spleen and thymus. Statistical analysis was performed using the unpaired t test.

The following terms are used in the present application:

The terms "treat," "treatment," and "treating," as used herein, refer to alleviating, ameliorating, stabilizing, delaying onset, or abrogating a disease, disorder, and/or symptoms thereof.

The terms "prevent," "prevention," and "preventing," as used herein, refer to prophylactically avoiding the development of a disease, disorder, and/or symptom thereof.

"T-cell-mediated autoimmune disease," as used herein, means a disease in which the T cells in the immune system attack self proteins, causing tissue damage. T-cell mediated autoimmune diseases include, but are not limited to, type 1 diabetes, multiple sclerosis, rheumatoid arthritis, psoriasis, collagen II arthritis, autoimmune neuritis, systemic lupus erythematosus, Sjogren's disease, thyroid disease, sarcoidosis, autoimmune uveitis, matory bowel disease (Crohn's and ulcerative colitis), and autoimmune hepatitis.

"Therapeutically effective amount," as used herein, means an amount of soluble CD137 or CD137$^{pos}$ regulatory T cells which treats or prevents symptoms associated with a T-cell-mediated autoimmune disease.

"Soluble CD137," as used herein, refers to a form of CD137 which differs from full-length CD137 in that exon 8 has been spliced out. In one embodiment, soluble CD137 is recombinantly produced. In a specific embodiment, soluble CD137 is recombinantly produced via lentivirally-transduced HEK293 cells.

The present invention is directed toward therapeutic methods and compositions effective in treating or preventing T-cell-mediated autoimmune diseases. In particular, soluble CD137 and CD137-expressing Treg cells are effective in mediating the progression of T-cell-mediated autoimmune disorders such as type 1 diabetes (T1D).

Because of the need for an effective therapeutic, T1D is actively studied in humans and mice, the latter by the use of mouse modeling systems. Non-obese diabetic (NOD) mice are used as a representative animal model of T1D. In mice, the B10 Cd137 allele differs from the NOD CD137 allele at three exonal single nucleotide polymorphisms (SNPs). Kachapati, K. et al., *The NOD mouse model of Type one diabetes, Animal Models of Diabetes Research, Methods Mol. Biol.* 933:3-16 (2012).

CD137$^{pos}$ Tregs are a functionally superior Treg subset characterized by surface expression of CD137, but also by alternate splicing and production of soluble CD137 which can directly suppress CD4$^{pos}$ T cell activation. Mice expressing the B10 CD137 haplotype, compared to NOD CD137 haplotype, show increased peripheral survival of functionally superior CD137$^{pos}$ Tregs. Thus, is Treg expressing CD137 regulates one of the mechanisms of type 1 diabetes.

The pro-survival members of the TNFR family such as CD137 are known to signal through a family of signaling adapter protein known as TRAFs. Upon receptor signaling, the TRAF1 and TRAF2 are recruited to the conserved TRAF-binding motifs in the cytoplasmic tails of CD137. The association of TRAF2 with cell membrane (insoluble fraction) in anti-CD137 treated CD137$^{pos}$ Tregs confirms that the antibody signals intracellularly through CD137. This is consistent with the previous observation that CD137 co-stimulation initiates survival of T cells by signaling through TRAF1 and TRAF2 adapter proteins linked to downstream kinase cascades which phosphorelates NF-KB and AP-1.

Upregulation of another downstream signaling molecule, Bcl-xl, in anti-CD137 treated CD137$^{pos}$ Tregs was also observed. Previous studies have also shown that CD137 co-stimulation leads to upregulation of pro-survival molecule Bcl-xl, resulting in expression of survival and effector genes in T cells. The presently disclosed data confirms that anti-CD137 antibody specially targets CD137 expressing CD4$^{pos}$CD25$^{pos}$ Tregs and initiates a downstream signaling cascade.

Anti-CD137 antibody treatment increases the number of CD4$^{pos}$CD25$^{pos}$ T cells in NOD mice and anti-CD137 antibodies bind specifically to CD4$^{pos}$CD25$^{pos}$ Tregs in vivo. Irie, J. et al., *Modulating Protective and Pathogenic CD4+ Subsets via CD137 in type one diabetes, Diabetes* 56(1):186-96 (2007). The instant data shows superior survival of Tregs expressing the B10 CD137 haplotype both in vivo and in a mixed bone marrow chimera system. The B10 Cd137 allele differs from the NOD allele at three exonal SNPs. These sequence polymorphisms have been shown to mediate decreased cell signaling by the NOD allele, and it is known that CD137 signaling enhances Bcl-xl production which mediates cell survival. This shows that increased survival is correlated with increased CD137$^{pos}$ Treg Bcl-xl and Bcl2 production by CD137$^{pos}$ Tregs with the B10 allele in bone marrow chimera mice and that increased cell survival is a cell intrinsic feature of CD137 in CD137$^{pos}$ Tregs.

The instantly disclosed data also shows that anti-CD137 treatment does not alter Foxp3, IL-10 and TGF-β mRNA levels on CD4$^{pos}$CD25$^{pos}$CD137$^{pos}$ T cells before and after treatment. Furthermore, IL-2 cultured CD137$^{pos}$ Tregs produced significantly high levels of soluble CD137 from anti-CD137 treated versus untreated mice. Previously, it has been shown that CD137$^{pos}$ Tregs from untreated mice proliferate upon IL-2 culture in vitro. Kachapati, K., et al., The B10 Idd9.3 *Locus Mediates Accumulation of Functionally Superior CD137+ Regulatory T Cells in the Nonobese Diabetic Type 1 Diabetes Model, J. Immunol.* October 12. (Epub ahead of print) (2012).

Soluble CD137 also significantly increased in NOD serum after anti-CD137 treatment. Although we have previously observed soluble CD137 from untreated CD137$^{pos}$ Tregs after IL-2 culture in vitro, it is undetectable in untreated NOD serum. Previously, anti-CD137 antibody treatment increased the frequency of CD4$^{pos}$CD25$^{pos}$ Tregs (Irie, et al.). Hence, increase in serum soluble CD137 after treatment may result from both the increase in Tregs and the increased production of soluble CD137 from CD137$^{pos}$ Tregs after treatment. The increased levels of soluble CD137 in vivo after treatment may also result from accumulation of soluble CD137-anti-CD137 antibody complex formation. This accumulation increases the half-life of soluble CD137 in the serum, which normally would have been removed by catabolism or by binding to the CD137 ligand. However, the significant increase in soluble CD137 production by CD137$^{pos}$ Tregs after antibody treatment indicates that the increase in serum soluble CD137 is not wholly due to increased half-life of soluble CD137. The presence of soluble CD137 is linked with an attempt to regulate over-activation of the immune system (Liu, G. Z., et al., *Decreased 4-1BB expression on CD4+CD25 high regulatory T cells in peripheral blood of patients with multiple sclerosis*. Clin Exp Immunol, 154(1):22-9 (2008); Polte, T., et al., CD137 *ligand prevents the development of T-helper type 2 cell-mediated allergic asthma by interferon-gamma-producing CD8+* T cells. Clin Exp Allergy, 37(9):1374-85 (2007)). Similarly, the increased production of soluble CD137 may also be an essential mechanism for protective anti-CD137 antibody treatment.

It has been previously reported that Foxp3$^{pos}$TGF-β$^{pos}$ T cells significantly decline with age in NOD mice and that the aged CD4$^{pos}$CD25$^{pos}$ T cells become less suppressive against aged CD4$^{pos}$CD25$^{neg}$ T cells. The reduced number of CD137$^{pos}$ Tregs in NOD mice with age can result in reduced peripheral immune regulation with age in NOD mice. It is important to note that the amount of CD137 (MFI) on the cell surface of CD4$^{pos}$CD25$^{pos}$ Tregs is not decreased on aged NOD CD137$^{pos}$ Tregs—the surviving CD137$^{pos}$ Tregs are all CD137-high expressors. Rather, there is a decrease in cellular CD137 expression in young NOD vs. NOD.B10 Idd9.3 CD137$^{pos}$ Tregs, which likely affects the number of surviving cells long term. Decreased expression of an allele that in itself mediates decreased signaling can combine to produce an intrinsically mediated decreased long term survival of these cells. This is entirely consistent with studies of the function of CD137 in CD137 knockout mice, which have decreased long term survival of antigen specific CD8 T cells. Since CD137$^{pos}$ Tregs are functionally superior at regulation, a decrease of this cell subset over time can result in decreased peripheral regulation and increased risk of autoimmunity. The data shows that CD137 co-stimulation is important for Treg-mediated diabetes treatment and prevention.

Mouse CD4$^{pos}$CD25$^{pos}$ Tregs have been differentiated into subsets based on their expression of cells surface molecules such CD134, integrin alpha E beta 7, and CD62L, which varies their suppressor activity, or molecules such as CD45RA$^{pos}$ and P-selectin, which delineate Treg differentiation in vitro or in vivo. Herein, two sub-populations of CD4$^{pos}$CD25$^{pos}$ Tregs, CD137$^{pos}$ and CD137$^{neg}$, are differentiated. These subsets are not merely phenotypically differentiated by cell surface expression of CD137, but by differences in functional cell-mediated suppression, and critically, by differences in the production of immunosuppressive soluble CD137. The production of soluble CD137 makes the CD137$^{pos}$ Tregs superior suppressors. Notably, under in vitro culture conditions, CD137$^{neg}$ Tregs can be converted to CD137$^{pos}$ Tregs that also produce soluble CD137. Cultured Tregs have been shown to be functionally superior to uncultured Tregs, and it is shown by the invention that CD137 production could partially mediate this superior suppression. Although it has been shown that CD137$^{pos}$ Tregs are present in the thymus and thus some unknown percentage are "natural" Tregs, the ability to convert CD137$^{neg}$ Tregs to CD137$^{pos}$ Tregs also shows that under conditions of an immune response Tregs may become induced CD137$^{pos}$ Tregs.

Soluble CD137 has been reported in the sera of rheumatoid arthritis (RA) patients and in the cerebrospinal fluid (CSF) of multiple sclerosis (MS) patients and MS patients have decreased expression of CD137 on their Tregs. In addition, soluble CD137 has been reported to arise later in the immune response. While not desiring to be bound by theory, it is believed that soluble CD137 can act as a "brake" upon normal immune activation. In this scenario, antigen specific T effectors can initially upregulate CD137 and stimulate CD137L on antigen presenting cells (APCs) and possibly on other T cells. Activation of antigen specific Tregs by the same conditions would then produce soluble CD137, which can interrupt the immune activation of both T cells and APCs expressing CD137L. Insufficient production of soluble CD137 (for example, in the system, mediated by a decrease in survival of Tregs producing soluble CD137 with age) can lead to exaggerated immune activation. Although CD137L signaling in monocytes, B cells and dendritic cells (DCs) can cause activation, CD137L cross-linking with immobilized CD137 is essential for this process and hence it is shown that, in contrast, soluble CD137 can suppress these subsets of cells in vivo. Although CD137$^{neg}$ Tregs can be converted to CD137$^{pos}$, this takes more time, and these cells always produce less soluble CD137 in the system (FIGS. 7*b*, 8*b*). Thus, a quantitative deficiency of CD137$^{pos}$ Tregs can enhance autoimmunity with age. The data supports the conclusion that enhancing site specific expression of soluble CD137 can downregulate autoimmunity.

Figure 14:
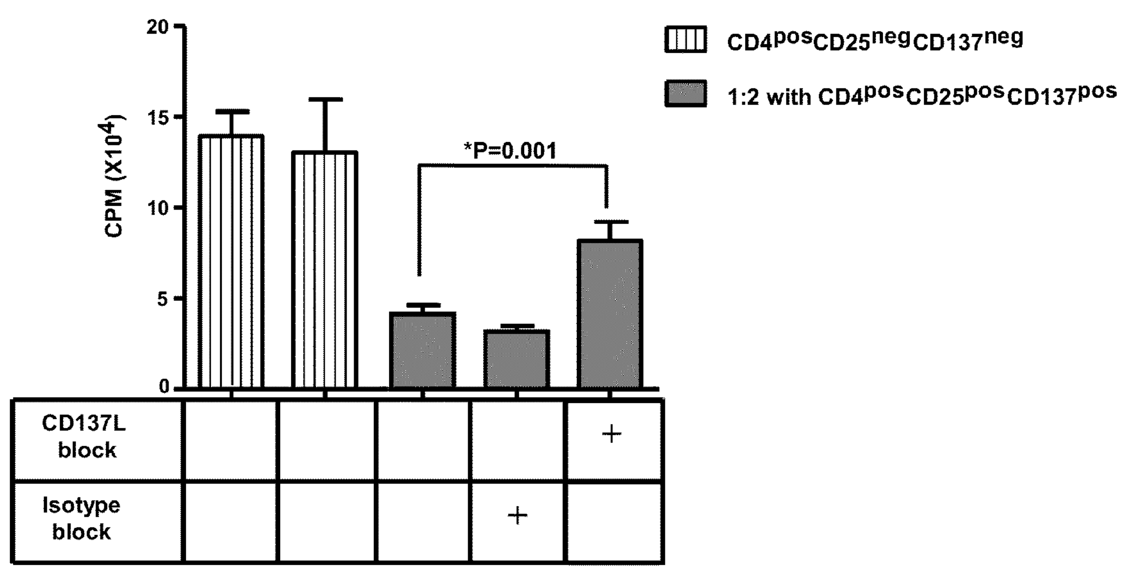
FIG. 14 shows that blockade of CD137L abrogates soluble suppression mediated by $CD137^{pos}$ Tregs. NOD $CD4^{pos}CD25^{neg}CD137^{neg}$ and $CD4^{pos}CD4^{pos}CD137^{pos}$ T cells were sorted from 5-7 week old NOD mice. 100,000 $CD4^{pos}CD25^{neg}CD137^{neg}$ T cells were plated in the bottom of a 96 well transwell plate with 50,000 $CD4^{pos}CD25^{pos}CD137^{pos}$ T cells in the top well. 50,000 CD3/CD28 beads were added to the bottom and to the top of the plate. 20 μg/ml of CD137 ligand blocking antibody (n=4 experiments) or IgG2a isotype antibody (n=3 experiments) were added to the bottom wells. The cells were pulsed with $^3$H labeled thymidine on day 3 and harvested after 16 hours. Statistical analysis was performed using the unpaired t test.

To understand the role of soluble CD137 in diabetes protection, the role of soluble CD137 was assessed in vitro. Previously we have seen that CD137$^{pos}$ Tregs are highly suppressive in a contact independent system in vitro (Kachapati, et al., *J. Immunol*.). Here, CD137L blockade experiment showed that CD137$^{pos}$ Tregs suppress through soluble CD137 in a contact independent system. Also, CD137L blockade alone had no effect the proliferation of CD4$^{pos}$CD25$^{neg}$CD137$^{neg}$ T cells, suggesting that T:T cell CD137-CD137L co-stimulation did not play a significant role in proliferation in our system. (FIG. 14). It has also been shown that soluble CD137 binds to CD137L in vitro (Shao, Z., et al., *Characterisation of soluble murine CD*137 *and its association with systemic lupus, Mol. Immunol.* 45(15): 3990-9 (2008)). Expression of CD137L is tightly regulated, such that low levels of CD137L expression on CD4 T cells has been detected (data not shown), similar to the results published by another group (Polte, T., et al., *CD*137 *ligand prevents the development of T-helper type* 2 *cell-mediated allergic asthma by interferon-gamma-producing CD*8+ *T cells, Clin. Exp. Allergy,* 37(9):1374-85 (2007)). Thus, in vitro culture conditions showed that soluble CD137 actively suppresses the proliferation of CD4$^{pos}$CD25$^{neg}$CD137$^{neg}$ T cells and does not simply act by passive blockade of the CD137-CD137L interaction.

To directly test the function of soluble CD137, an in vitro system for production and purification soluble CD137 was designed. Eukaryote cell lines were transduced with lentiviral vector containing soluble CD137 construct for production of soluble CD137 in vitro. Western blot (under reducing and non-reducing conditions) and a more precise analytical ultracentrifugation (AUC) were used to characterize the protein conformation of soluble CD137. Structurally, it was shown that soluble CD137 primarily exists as a 54.3 kDa dimer and a small fraction exists as 26.9 kDa monomer with two possible glycosylation sites and a disulfide bond. Our results are similar to the previous finding that CD137 is a homodimer at ~55 kDa and a monomer at ~35 kDa (Shao, Z., et al., *Characterisation of soluble murine CD*137 *and its association with systemic lupus, Mol. Immunol.* 45(15):3990-9 (2008); Kwon, B. S., et al., *Genomic organization and chromosomal localization of the T-cell antigen* 4-1*BB, J. Immunol.* 152(5): 2256-62 (1994)). It also matches the predicted protein sequence of soluble CD137 protein (Pubmed—Protein search/NCBI Conserved Protein Domains). Analytical ultracentrifugation showed that 12% of purified soluble CD137 formed different multimeric forms. The presently disclosed and characterized purified soluble CD137 is believed to be the first recombinantly produced purified soluble CD137.

Purified soluble CD137 was then used for functional characterization of the protein. Results showed that the purified soluble CD137 is functionally active and reduced CFSE dilution and cell cycle progression in CD4 T cells in vitro. This supports the observation that blockade of CD137L abrogates the suppression of CD4 T cells through soluble CD137 produced by Tregs (FIG. 14). Tests showed that soluble CD137 is non-toxic to cells and does not cause activation induced cell death (AICD) (data not shown). It has been shown that soluble CD137 inhibits T cell proliferation and that soluble CD137 arises later in the immune response to prevent excessive immune activation (Michel, J. and H. Schwarz, *Expression of soluble CD*137 *correlates with activation-induced cell death of lymphocytes, Cytokine* 12(6): 742-46 (2000)). The presently disclosed data confirms that soluble CD137 is suppressive to CD4 T cells in vitro (FIG. 14). As shown before, soluble CD137 suppression is mediated through CD137L. As other members of TNF and TNFR family, CD137L also undergoes reverse signaling. CD137L signaling has been shown to cause activation in APC (macrophages, B cells, monocytes), but its role on T cells is not well established. Interestingly, studies have shown that cross-linking CD137L with plate bound recombinant CD137-Fc is essential for monocyte activation and that soluble form of the receptor does not elicit similar signal (Langstein, J., et al., *CD137 (ILA/4-1BB), a member of the TNF receptor family, induces monocyte activation via bidirectional signaling, J. Immunol.* 160(5):2488-94 (1998)). These studies indicate that the biochemical nature of the ligand binding may vary between the surface bound CD137 to soluble CD137.

Furthermore, the presently disclosed data shows that soluble CD137 treatment significantly reduces the incidence of diabetes in NOD mice, which shows that soluble CD137 is immunosuppressive in vivo. This also explains the mechanism for anti-CD137 antibody-mediated diabetes protection, since the treatment increases soluble CD137 production. While not desiring to be bound by theory, it is believed that after treatment, anti-CD137 antibody binds to Tregs in vivo, which then produces high levels of soluble CD137. The increase in soluble CD137 after treatment causes a quantitative increase in total suppression against pathogenic effector cells. This downregulation of autoimmune activation may prevent diabetes. Hence, treatment with anti-CD137 antibody activates a positive feedback loop that increases the expression of soluble CD137. This in-turn is important for suppressing pathogenic effectors during diabetes progression. In vivo, soluble CD137 may suppress pathogenic T cells by directly initiating negative signaling through CD137L or indirectly by blocking T:T CD137-CD137L interaction or both. Since CD137L blockade experiment did not abrogate the proliferation of CD4 T cells, the indirect suppression through CD137-CD137L blockade between T cells is not true for our in vitro system. However, in vivo soluble CD137 can bind to CD137L expressing APC and activated T cells and further prevent CD137 co-stimulation of pathogenic cells. Hence, the instantly disclosed data unveils the mechanism by which anti-CD137 treatment protects against diabetes. The presently disclosed data establishes soluble CD137 as a novel mechanism by which T regulatory cells suppress, and more importantly, can induce immunoregulation of pathogenic effectors cells to avert the incidence of diabetes.

Moreover, results show that both soluble CD137 and CD137 expressing Treg cells are effective in mediating the T cell mediated pathway underlying the physiological mechanisms of autoimmune diseases, and in particular, type 1 diabetes.

Results confirm that the purified soluble CD137 has a biological effect in vivo. The data establish that $CD4^{pos}CD25^{pos}$ T cells are essential for anti-CD137 antibody-mediated diabetes protection because elimination of $CD4^{pos}CD25^{pos}$ T cells by anti-CD25 antibody before anti-CD137 treatment abrogates disease protection. Anti-CD137 antibody mediated its diabetes protection through $CD4^{pos}CD25^{pos}CD137^{pos}$ T cells (anti-CD137 antibody bound to $CD4^{pos}CD25^{pos}$ T cells). The Tregs bound to anti-CD137 in vivo produce high levels of soluble CD137 in culture in vitro. Anti-CD137 treatment also increases soluble CD137 in serum. Moreover, protective anti-CD137 treatment increased alternately spliced soluble form of CD137 from $CD4^{pos}CD25^{pos}CD137^{pos}$ T cells in vitro. Furthermore, blockade of CD137L diminished the superior function of $CD4^{pos}CD25^{pos}CD137^{pos}$ T cells in a transwell plate, indicating that soluble CD137 produced has suppressive properties. Purified soluble CD137 also delays the incidence of diabetes in NOD mice.

The results indicate that soluble CD137 is a novel immunosuppressive molecule produced by T regulatory cells and is capable of inducing immunoregulation of pathogenic effector cells to avert the incidence of diabetes. Anti-CD137 antibody treatment mediates its protection through soluble CD137, which by itself is therapeutic for T1D and other T-cell-mediated autoimmune diseases. Since all the effector T cells in these diseases express the CD137 ligand upon activation, all T-cell-mediated autoimmune diseases are susceptible to treatment methods with soluble CD137 and $CD137^{pos}$ regulatory T cells, according to the methods and compositions disclosed herein.

Pharmaceutical Compositions

The present invention further provides a pharmaceutical composition for use in the treatment or prevention of T-cell-mediated autoimmune diseases comprising as the active agent soluble CD137 or $CD137^{pos}$ regulatory T cells, together with a pharmaceutically acceptable carrier thereof and optionally other therapeutic agents. The carrier must be "acceptable" in the sense of being compatible with the other ingredients of the formulation and not deleterious to the recipients thereof. The invention further includes a pharmaceutical composition, in combination with packaging material suitable for the pharmaceutical composition, including instructions for the use of the pharmaceutical composition in the treatment or prevention of T-cell-mediated autoimmune diseases.

Compositions include those suitable for parenteral administration. In a specific embodiment, the compositions disclosed herein are suitable for intravenous administration, although other specific means of parenteral administration are also viable (such as, for example, intra-arterial, intramuscular, or subcutaneous administration). The compositions may be prepared by any methods well known in the art of pharmacy, for example, using methods such as those described in *Remington: The Science and Practice of Pharmacy* (21st ed., Lippincott Williams and Wilkins, 2005, see Part 5: Pharmaceutical Manufacturing).

For parenteral administration, suitable compositions include aqueous and non-aqueous sterile suspensions for parenteral and/or intravenous administration. The compositions may be presented in unit dose or multi-dose containers, for example, sealed vials and ampoules.

As will be understood by those of skill in this art, the specific dose level for any particular patient will depend on a variety of factors, including the activity of the agent employed; the age, body weight, general health, and sex of the individual being treated; the time and route of administration; the rate of excretion; other drugs that have previously been administered; and the severity of the particular T-cell-mediated autoimmune disease undergoing therapy.

In one embodiment, a method of treating or preventing a T-cell-mediated autoimmune disease is provided, comprising administering to a mammal in need thereof a therapeutically effective amount of soluble CD137. In one embodiment, the soluble CD137 is recombinant CD137. In a specific embodiment, the recombinant soluble CD137 is produced by cells transduced with the construct set forth in FIG. 15*a*.

In a specific embodiment, the administering suppresses $CD4^{pos}$ non-regulatory T cells, thereby treating or preventing the T-cell-mediated autoimmune disease. In a further embodiment, the method comprises the additional steps of monitoring disease progression and repeating administration of said soluble CD137 one or more times, thereby treating or preventing the T-cell-mediated autoimmune disease. In another embodiment, the mammal is a mouse or a human.

In another embodiment, a method treating or preventing a T-cell-mediated autoimmune disease is provided, comprising administering to a mammal in need thereof a therapeutically effective amount of CD137$^{pos}$ regulatory T cells. In a specific embodiment, the administering suppresses CD4$^{pos}$ non-regulatory T cells, thereby treating or preventing the T-cell-mediated autoimmune disease. In a further embodiment, the method comprises the additional steps of monitoring disease progression and repeating administration of said CD137$^{pos}$ regulatory T cells one or more times, thereby treating or preventing the T-cell-mediated autoimmune disease. In another embodiment, the mammal is a mouse or a human.

Disease progression can be monitored in a variety of ways known to the skilled clinician. In the case of type 1 diabetes, disease progression can be monitored by assessing blood glucose levels, C-peptide levels, or glucose tolerance testing. In the case of other T-cell-mediated autoimmune diseases, such as multiple sclerosis, rheumatoid arthritis, psoriasis, or others, disease progression can be monitored by assessing clinical symptoms. In one embodiment, if the appropriate assessments indicate the autoimmune disease is advancing or has not yet responded to treatment (as evidenced by abnormal blood glucose levels or clinical signs of disease progression), the clinician can administer an additional dose of soluble CD137 or CD137$^{pos}$ regulatory T cells and re-assess disease progression. Successive rounds of administering soluble CD137 or CD137$^{pos}$ regulatory T cells, coupled with monitoring disease progression, may be needed in order to achieve the desired treatment or prevention of the T-cell-mediated autoimmune disorder.

In another embodiment, a pharmaceutical composition for the treatment or prevention of a T-cell-mediated autoimmune disease is provided, the pharmaceutical composition comprising: a therapeutically effective amount of soluble CD137; and a pharmaceutically-acceptable carrier. In one embodiment, the pharmaceutical composition is in the form of an injectable suspension. In another embodiment, the pharmaceutical composition is administered parenterally. In a more specific embodiment, the pharmaceutical composition is administered intravenously.

In another embodiment, a pharmaceutical composition for the treatment or prevention of a T-cell-mediated autoimmune disease is provided, the pharmaceutical composition comprising: a therapeutically effective amount of CD137$^{pos}$ regulatory T cells; and a pharmaceutically-acceptable carrier. In one embodiment, the pharmaceutical composition is in the form of an injectable suspension. In a specific embodiment, the pharmaceutical composition is administered parenterally. In a more specific embodiment, the pharmaceutical composition is administered intravenously.

The methods and compositions disclosed herein are suitable for use in autoimmune diseases mediated by T-cells. In some embodiments, the T-cell-mediated autoimmune disease is selected from the group consisting of type 1 diabetes, multiple sclerosis, psoriasis, and rheumatoid arthritis. In more specific embodiments, the T-cell-mediated autoimmune disease is type 1 diabetes.

EXAMPLES

The following examples are given by way of illustration and are in no way intended to limit the scope of the present invention.

Example 1

Materials and Methods

The following materials and methods were used in the preparation of the examples embodying some aspects of the subject invention.

Mice and Reagents

NOD, NOD.B10 Idd9.3, and NOD.B6-Ptprc (hereafter referred to as "NOD.CD45.2") mice were maintained under specific pathogen-free conditions in the animal facilities. Mice were handled in accordance with the institutional animal care guidelines. Urinary glucose analysis was performed using Tes-tape (Shionogi, Osaka Japan) once a week. Agonist anti-CD137 monoclonal antibody (clone 3H3) was a gift from Dr. R. Mittler (Emory University, Atlanta, Ga.). Antibodies against mouse 2.5G2-Fc, CD4-APC, CD4-APC-Cy7, CD25-PerCP-Cy5.5, CD25-FITC, Strepavidin-PE, and Strepavidin-APC were purchased from BD Biosciences (San Jose, Calif.). Anti-mouse CD137L (clone TSK-1) blocking antibodies or IgG2a isotype control (clone RTK2758) antibodies were from BioLegend (San Diego, Calif.). CD3/CD28 coated beads and recombinant mouse IL-2 were from Invitrogen (Grand Island, N.Y.). CD137-Fc conjugated recombinant protein was purchased from R&D Systems (Minneapolis, Minn.). Primers for Gapdh (4352339E-0801016), Beta-2 microglobulin (Mm00437762_m1), Foxp3, IL-10, TGF-β, and Bcl-xl were purchased from Applied Bioscience (Mumbai, India). Custom designed primers were used for membrane bound and soluble CD137 (Applied Bioscience). For membrane bound CD137, the forward primer is CCCCCTGTGGTGAGCTTC (SEQ ID NO: 1) and the reverse primer is AGGAGGGCACTCCTTGCA (SEQ ID NO: 2). For soluble CD137, the forward primer is CCCCCTGTGGTGAGCTTC (SEQ ID NO: 3) and the reverse primer is GGGAGGACCAGCATTTAAGAAGA (SEQ ID NO: 4). The probe for both the primers is TCCCAGTACCACCATT (SEQ ID NO: 5).

Anti-CD137 Treatment

NOD mice were treated with 330 μg of anti-CD25 antibody or PBS twice at a one week interval. One day after the second injection, the mice were either untreated or treated three times with 200 μg of anti-CD137 at 3-week intervals. The mice were tested for glucososuria each week. Diabetes was confirmed when blood glucose levels were >300 mg/dl. For analyzing Tregs after anti-CD137 treatment, the mice were treated with 100 μg of anti-CD137 twice at a one week interval and sacrificed for analysis one day after the second treatment.

Flow Cytometry

For staining CD137, NOD and NOD.B10 Idd9.3 splenocytes or thymocytes were extracted and incubated with 2.5G2 Fc block. For FACS analysis, cells were then stained with CD4-APC, CD25-FITC, and stained for CD137 using IgG2a anti-CD137 or IgG2a isotype, then anti-IgG2a biotin and strepavidin-PE. (NOD.CD45.2×NOD.B10 Idd9.3) F1 spleen and pancreatic lymph node were stained with CD4-APC-Cy7, CD25-Percp-Cy5.5, CD45.1-FITC, CD45.2-APC and CD137-PE or IgG2a isotype-PE. All Facs data was analyzed using FlowJo (Treestar, Oreg.).

Bone Marrow Chimera 9-13 week old (NOD.CD45.2×NOD.B10 Idd9.3) F1 mice were irradiated with 800-1200 Rads. 15-25 million bone marrow cells from 5-12 week old NOD.B10 Idd9.3 and NOD.CD45.2 mice were extracted without RBC lysis. Mature CD4, CD8 and CD90 cells were removed using magnetic beads (Miltenyi Biotech, Auburn, Calif.) and the bone marrow was then mixed at a 1:1 ratio and injected into the irradiated F1 mice. Recipient mice were given water treated with antibiotic (neomycin prisulfate salt hydrate) for two weeks after transfer. The recipient F1 mice were tested for glucososuria each week and sacrificed 12-20 week post injection for analysis of peripheral cell populations by FACS.

RT-PCR

CD4 T cells were extracted from splenocytes using CD4 magnetic beads (Miltenyi Biotech). The CD4 T cells were blocked with 2.5G2 and stained with CD4-APC, CD25-FITC, and anti-CD137-APC. The cells were sorted using a BD FacsAria machine (BD Bioscience) into $CD4^{pos}CD25^{neg}CD137^{neg}$, $CD4^{pos}CD25^{pos}CD137^{neg}$, and $CD4^{pos}CD25^{pos}CD137^{pos}$ cell subsets, RNA was extracted from the sorted cells using an RNeasy mini kit (Qiagen, Valencia, Calif.) and converted into cDNA (Promega Reverse Transcription System, Madison, Wis.). Quantitative Real Time Polymerase Chain Reaction (RT-PCR) was performed on the cDNA using primers for Gadph, Foxp3, IL-10, TGF-β, Bcl-xl, B2m, soluble CD137 and membrane bound CD137 using a StepOnePlus Real-Time PCR system (Applied Biosystems). The CT values of the gene of interest were subtracted from the CT of the housekeeping gene (Gadph or B2m) and the data graphed using GraphPad Prism 5 (Version 5.02).

Treg Suppression Assay

The $CD4^{pos}CD25^{neg}CD137^{neg}$, $CD4^{pos}CD25^{pos}CD137^{neg}$, and $CD4^{pos}CD25^{pos}CD137^{pos}$ splenocytes were stained and sorted using BDAria (BD Bioscience). 50,000 $CD4^{pos}CD25^{neg}CD137^{neg}$ T cells were cultured in U-bottom 96 well plate with 1 μg/well soluble anti-CD3, 50,000 irradiated splenocytes (1500 rads) and varying numbers of $CD4^{pos}CD25^{pos}CD137^{neg}$ or $CD4^{pos}CD25^{pos}CD137^{pos}$ Tregs. In some cultures 50,000 $CD4^{pos}CD25^{neg}CD137^{neg}$ T cells were cultured with 20,000 CD3/28 beads in triplicate with increasing concentration of soluble CD137-Fc. 20 μg/ml of either CD137L blocking antibodies or IgG2a isotype control antibodies were added to some wells. All cells were cultured at 37° C. with 5% $CO_2$ and pulsed with 1 μCi [$^3$H] thymidine on Day 3, 16 hours before harvest. On Day 4, thymidine incorporation was assessed using a beta scintillation counter.

Treg Transwell Suppression Assay 100,000 sorted $CD4^{pos}CD25^{neg}CD137^{neg}$ T cells were cultured with 100,000 irradiated splenocytes (1500 rads) and 1.25 ug/ml soluble anti-CD3 in the bottom wells of a 96 well transwell plate. 25,000 or 50,000 $CD4^{pos}CD25^{pos}CD137^{neg}$ or $CD4^{pos}CD25^{pos}CD137^{pos}$ Tregs were cultured in the top wells with 100,000 irradiated (1500 rads) splenocytes. In some cases, the cells in the bottom wells were cultured with 50,000 CD3/CD28-coated beads (Invitrogen) in the absence of APCs. The cells were cultured at 37° C. in 5% $CO_2$ and were pulsed with 1 μCi thymidine on Day 3. The cells in the bottom wells were harvested and counted using a beta scintillation counter.

ELISA

Mouse 4-1BB DuoSet Elisa system (R&D Systems) was used to detect soluble CD137 from serum and culture supernatants. The kit uses rat anti-mouse 4-1BB capture antibody and biotinylated goat anti-mouse 4-1BB detection antibody. Recombinant mouse 4-1BB, provided in the kit, was used as a standard.

Treg Culture 50,000 $CD4^{pos}CD25^{pos}CD137^{neg}$ or $CD4^{pos}CD25^{pos}CD137^{pos}$ Tregs were cultured in 96 well U-bottom plate with 25 U/ml mouse recombinant IL-2 alone with or without 1.25 μg/ml of anti-CD3 antibody for 5 days, and the supernatants were tested for soluble CD137 as above by ELISA.

Production of Soluble CD137 Protein

The sequence-verified bacterial cDNA clone for *Mus musculus* soluble CD137 (B10 allele) was obtained from Open Biosystems (Clone ID 1497753). This cDNA was originally cloned into the pT7T3-Pac vector, flanked by unique EcoRI and NotI sites; (lacking in the CD137 coding sequence). By miniprep analysis it was confirmed that the soluble CD137 clone releases the expected ~916 bp fragment after digesting with EcoR1 and NotI. The soluble protein's coding sequence from pT7T3-Pac was excised and insert it into the multiple cloning site (MCS) of LeGO-iG2 using standard subcloning procedures. The B6 *Mus musculus* soluble CD137 cDNA coding sequence was inserted into the lentiviral vector, LeGO-iG2, downstream from the strong Spleen Focus-Forming Virus (SFFV) promoter between two unique restriction sites EcoRI and NotI. This location permits co-expression of sCD137 along with a downstream EGFP reporter gene, permitting green fluorescence to be used to monitor the efficiency of viral transduction and bicistronic protein expression. Mouse NIH3T3 fibroblasts and human embryonic kidney (HEK293) cells were transduced with VSVg-enveloped lentiviral particles made with either parent vector LeGO-iG2 or LeGO-iG2-sCD137. The resultant cell lines were cultured in 10.0% $CO_2$ at 37° C. and split as needed in IMDM media containing 10% fetal bovine serum (FBS). The supernatant from confluent cultures was collected over several weeks before each split and tested for the production of soluble CD137 by ELISA. Transduced NIH3T3 and HEK293 cells exhibiting stable EGFP expression were sorted for high (top 10%) and medium (middle 40-70%) expression using FACS Arial II flow cytometry. The sorted cell lines were subsequently re-plated and cultured for an additional five days in IMDM with 10% FBS before checking soluble CD137 expression by ELISA. Stable expressors were later used for protein purification and for freezing back producer stocks.

Purification of Soluble CD137

To purify soluble CD137 protein from culture supernatants, an anti-CD137 affinity chromatography column was generated. Anti-CD137 antibodies were first purified using 3H3 antibody/hybridoma. The antibody-producing cells were cultured in IgG-depleted FBS at $1\times10^6$ cells per flasks or in roller bottles, and split as required for 4 weeks. After this time period, the cells were serum-starved for two weeks to obtain optimal antibody production. The secreted antibody was then coupled to a CNBr-activated Sepharose™ 4B column (GE Life Sciences), according to the manufacturer's instructions. This results in strong covalent bound between the antibody and the beads. Coupling efficiency was assessed by running an elution buffer, i.e., 3.5M MgCl2, over the column. NanoDrop ND-1000 spectrophotometer was used to confirm that no CD137 antibody added was removed in the elution process. After elution, the soluble CD137 protein was dialyzed three times in Tris-Buffered Saline (TBS) and two times in PBS. The amount of purified soluble CD137 and degree of concentration was determined using a Ross Recorders spectrophotometer and ELISA.

Western Blot

The soluble CD137 protein samples were mixed in either 15 μL of reducing (10.0 ml 0.5 M Tris-HCl, 2.0 g SDS, 0.1 g Bromophenol Blue, 1.543 g of Dithiothreitol, 12.5 ml of 80% Glycerol, up to 50 ml with $H_20$) or non-reducing (10.0 ml 0.5 M Tris-HCl, 2.0 g SDS, 0.1 g Bromophenol Blue, 12.5 ml 80% Glycerol, up to 50 ml with $H_2O$) sample buffer. The samples were then boiled for 5 minutes and cooled to RT. 250 of each sample was loaded onto 12% Tris-gylycine gels (Novex) and run at 125V for 105 minutes in a XCell II apparatus (Invitrogen). Low molecular weight pre-stained protein markers (Invitrogen) were used as size controls. Transfer of protein onto nitrocellulose was next performed by electrophoresis at 25 V for 90 minutes. Afterwards, the blots were blocked using 10% BSA (Bovine Serum Albumin) in TBS-T (Tris-Buffered Saline with 2.0% Tween 20) for one hour and washed with 1×PBS. The primary antibody mouse IgG1 anti-CD137 (Santa Cruz clone 6D295) was added to the blots for one hour, followed by brief washing with PBS. Then, a polyclonal secondary antibody to mouse IgG-H&L (AP) (Invitrogen clone ab6729) was added for an hour and washed with PBS. The antibody-bound proteins were then stained using NBT (nitro-blue tetrazolium chloride) and BCIP (5-bromo-4-chloro-3'-indolyphosphate p-toluidine salt).

Data Analysis

All statistical analysis was performed using the unpaired T test or the Mann-Whitney test in GraphPad Prism 5 (Version 5.02). The survival analysis was performed using the log-rank test in GraphPad.

Example 2

Figure 6:
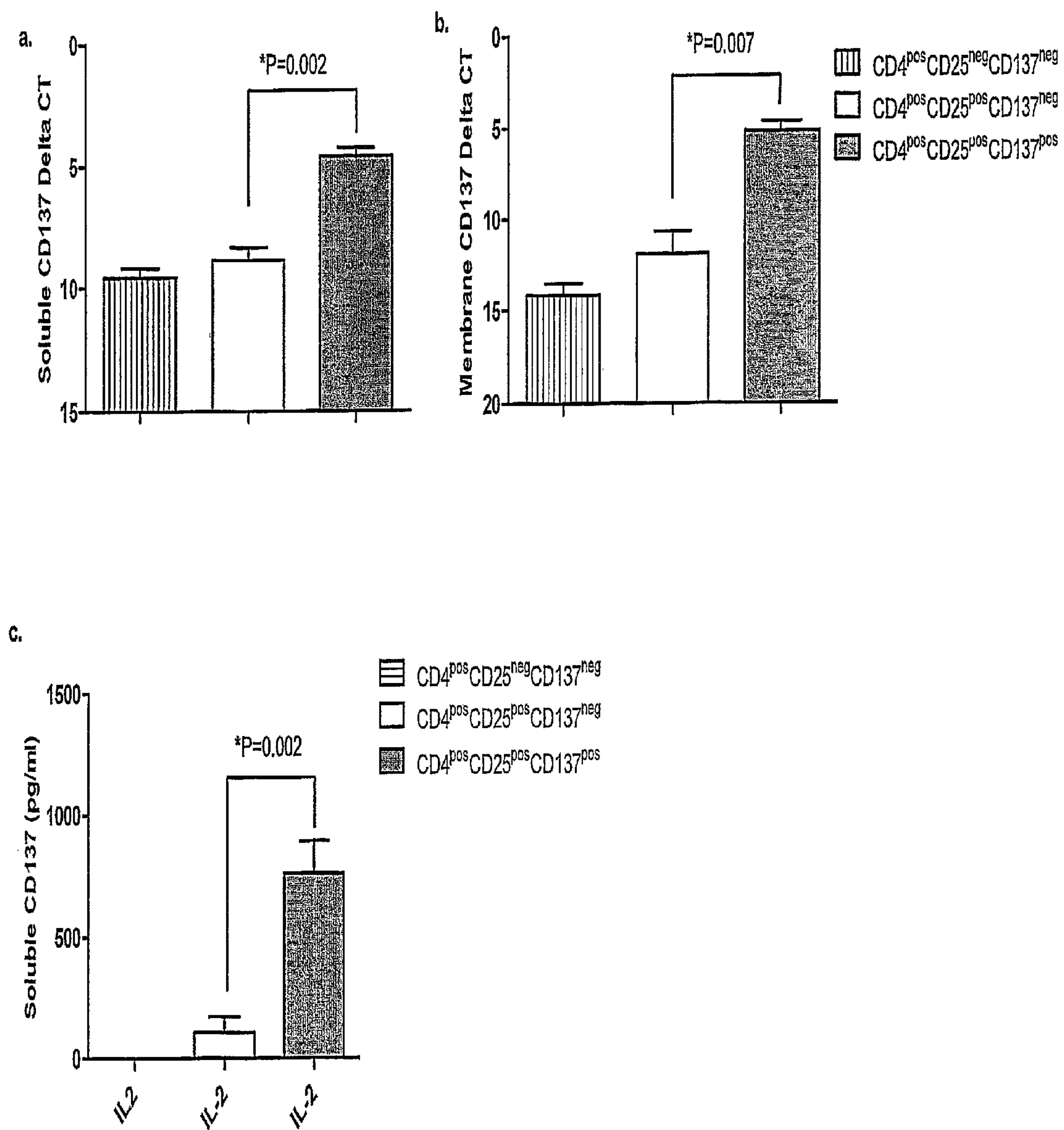
FIG. 6 shows $CD137^{pos}$ but not $CD137^{neg}$ Tregs produce soluble CD137 ex vivo. (a, b) NOD $CD4^{pos}CD25^{neg}CD137^{neg}$, $CD4^{pos}CD25^{pos}CD137^{neg}$, and $CD4^{pos}CD25^{pos}CD137^{pos}$ T cells were sorted from 4-8 wk old females. RNA was immediately extracted and converted to cDNA. RT-PCR was performed with a set of custom designed primers used to detect soluble (a) and membrane bound (b) CD137, both (n=3 experiments). B2m was used as an endogenous control. (c) NOD $CD4^{pos}CD25^{neg}CD137^{neg}$, $CD4^{pos}CD25^{pos}CD137^{neg}$, and $CD4^{pos}CD25^{pos}CD137^{pos}$ Tregs from 5-8 week mice were sorted. The cells were cultured in 96-well U-bottom plate with 25 U/ml IL-2 for 5 days. ELISA was performed on the supernatants for soluble CD137 (n=2 experiments). Statistical analysis was performed using the unpaired t test.
Figure 7:
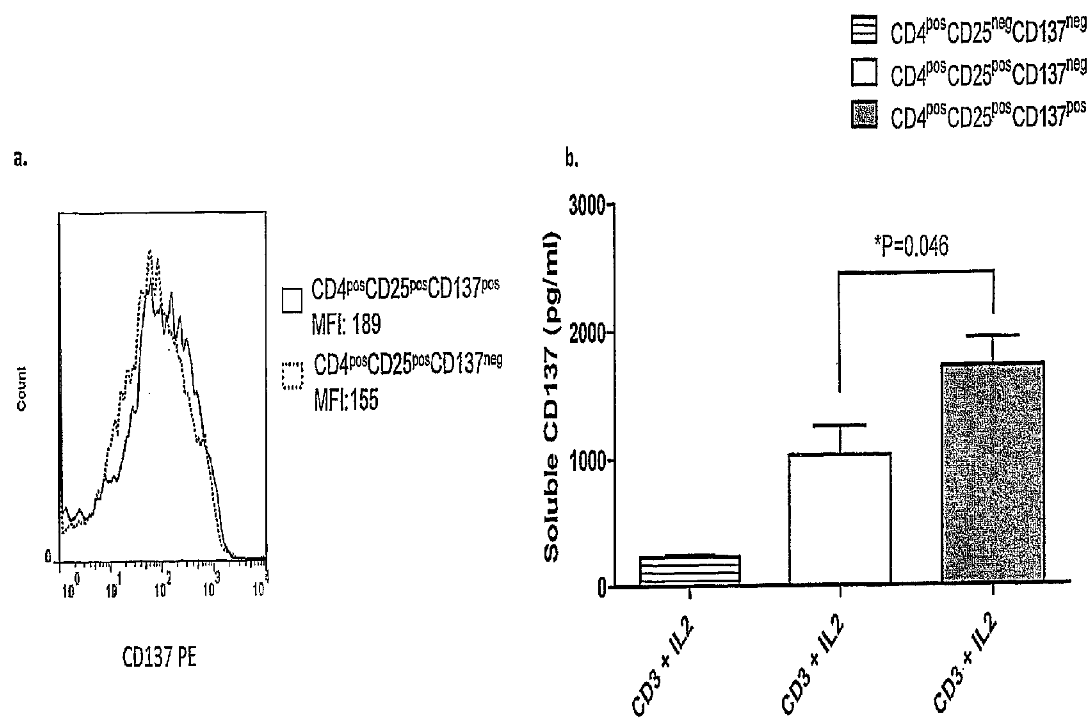
FIG. 7 shows $CD137^{neg}$ Tregs can convert into $CD137^{pos}$ Tregs and produce soluble CD137 upon anti-CD3 and IL-2 stimulation in vitro. (a) Five week NOD females were used for sorting $CD4^{pos}CD25^{pos}CD137^{neg}$ and $CD4^{pos}CD25^{pos}CD137^{pos}$ T cells and T cells were cultured. On day 5, the cells were stained with CD4-APC, CD25-FITC, and CD137-PE or matched isotype control. (b) NOD $CD4^{pos}CD25^{neg}CD137^{neg}$, $CD4^{pos}CD25^{pos}CD137^{neg}$, and $CD4^{pos}CD25^{pos}CD137^{pos}$ Tregs from 5-8 week female NOD mice were sorted. The cells were cultured in 96-well U-bottom plate with 25 U/ml IL-2 and 1.25 ug/ml of anti-CD3 for 5 days. ELISA was performed on their supernatants for soluble CD137 (n=4 experiments). Statistical analysis was performed using the unpaired t test.
Figure 8:
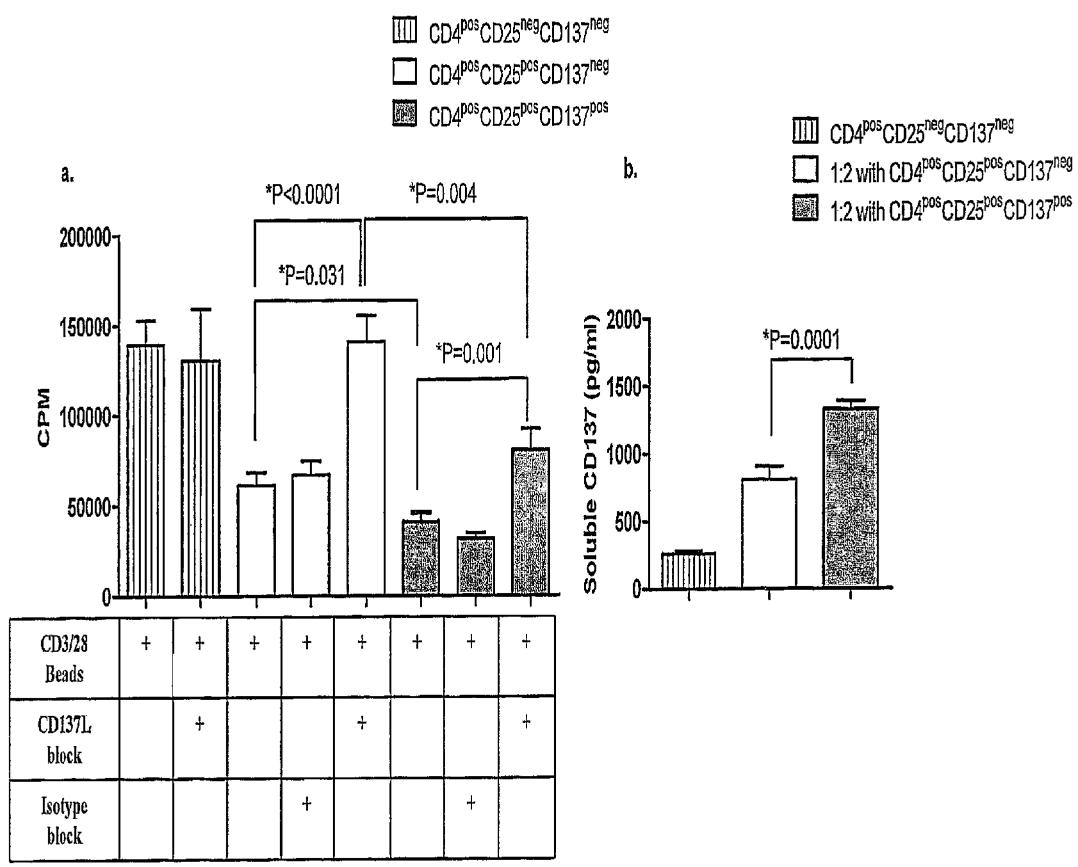
FIG. 8 shows that blockade of CD137L abrogates soluble suppression mediated by $CD137^{pos}$ Tregs in an APC independent transwell system. (a) NOD $CD4^{pos}CD25^{neg}CD137^{neg}$, $CD4^{pos}CD25^{pos}CD137^{neg}$, and $CD4^{pos}CD25^{pos}CD137^{pos}$ T cells were sorted from 5-7 week old NOD mice. 100,000 $CD4^{pos}CD25^{neg}CD137^{neg}$ T cells were plated in the bottom of a 96 well transwell plate with 50,000 $CD4^{pos}CD25^{pos}CD137^{neg}$ or $CD4^{pos}CD25^{pos}CD137^{pos}$ T cells in the top well. 50,000 CD3/CD28 beads were added to the bottom and top of the plate (n=5 experiments). 20 μg/ml of CD137 ligand blocking antibody (n=3 experiments) or in separate experiments, IgG2a isotype antibody (n=3 experiments) was added to the bottom wells. The cells were pulsed with $^3$H labeled thymidine on day 3 and harvested after 16 hours. Statistical analysis was performed using the unpaired t test. (b) NOD $CD4^{pos}CD25^{neg}CD137^{neg}$, $CD4^{pos}CD25^{pos}CD137^{neg}$, and $CD4^{pos}CD^{pos}CD137^{pos}$ T cells were sorted from 5-7 week old NOD mice. 50,000 $CD4^{pos}CD25^{neg}CD137^{neg}$ T cells were plated in U-bottom 96 well plates with 1.25 μg/well soluble anti-CD3, 50,000 irradiated (1500 rads) NOD splenocytes and 25,000 (1:2, n=5 experiments) of $CD137^{neg}$ or $CD137^{pos}$ Treg subsets. The supernatant was collected on day 5 and ELISA was performed on the supernatants for soluble CD137. Statistical analysis was performed using the unpaired t test.

As shown in FIGS. 6, 7 and 8, Tregs are the source of CD137: CD137$^{pos}$ Treg cells produce surface expressed CD137, as well as the isoform soluble CD137, while CD137$^{neg}$ Treg cells can be induced to produce the same isoforms.

RT-PCR primers were designed that discriminate soluble versus membrane bound CD137 and used to detect soluble CD137 versus membrane bound CD137 from freshly sorted NOD Treg subsets. CD137$^{pos}$ Tregs produced higher levels of soluble CD137 mRNA compared to CD137$^{neg}$ Tregs (FIG. 6*a*); CD4$^{pos}$CD25$^{neg}$CD137$^{neg}$ cells produced lower amounts of soluble CD137 under these conditions (FIG. 6*a*). Next the CD137$^{pos}$ and CD137$^{neg}$ Tregs were sorted from NOD mice and cultured with IL-2 alone (to allow survival in vitro). The CD137$^{pos}$ Tregs produce high levels of soluble CD137 compared to CD137$^{neg}$ Tregs; CD4 non-Treg cells did not produce soluble CD137 (FIG. 6*b*). Results demonstrate that CD137$^{pos}$ Tregs are the primary cellular source of soluble CD137.

To test whether CD137$^{neg}$ Tregs start expressing CD137 or producing soluble CD137 upon activation, CD137$^{pos}$ and CD137$^{neg}$ Tregs were sorted from NOD mice and cultured with IL-2 and anti-CD3. Notably, after 5 days of stimulation with IL-2 and CD3, CD137$^{neg}$ Tregs express similar levels of cell surface CD137 as CD137$^{pos}$ Tregs (FIG. 7*a*). The supernatants from the culture were also tested on day 5 for soluble CD137 and showed that stimulated CD137$^{neg}$ Tregs also produce soluble CD137, although less than CD137$^{pos}$ Tregs (FIG. 8*b*). These results demonstrate that CD3 and IL-2 stimulation causes CD137$^{neg}$ Tregs to express CD137 and initiate alternate splicing of Cd137 with subsequent production of soluble CD137 protein. Notably, however, non-Treg CD4$^{pos}$ cells did not produce significant amounts of soluble CD137 after stimulation under these conditions (FIG. 7*b*), supporting the finding that Tregs are the primary source of soluble CD137.

Example 3

Soluble CD137 Induces Suppression of Non-Treg CD4$^{pos}$ Cells

The production of soluble CD137 has been linked with decreased proliferation and increased cell death and DNA fragmentation in human PBMC and mouse splenocytes. Tests of whether the soluble CD137 produced by CD137$^{pos}$ Tregs could prevent proliferation of CD4 T cells in the in vitro transwell suppression assay were performed. To prevent any interaction of soluble CD137 with macrophages or dendritic cells, irradiated splenocytes were replaced with anti-CD3/CD28 coated beads in the in vitro suppression assay. It was observed that CD137$^{pos}$ Tregs were still more suppressive than CD137$^{neg}$ Tregs in a transwell assay using beads to stimulate T effector cells (P=0.031, FIG. 8*a*). CD137L blocking or isotype control antibody was used to test the effect of soluble CD137 produced by Tregs in transwell suppression. The presence of CD137L blocking antibody did not alter the proliferation of CD4$^{pos}$CD25$^{neg}$CD137$^{neg}$ T cells in the presence of CD3/CD28 beads (FIG. 8*a*). However, the blocking antibody abrogated suppression of both CD137$^{neg}$ and CD137$^{pos}$ Tregs (P=0.001), while the isotype antibody had no effect on suppression (FIG. 8*a*). The results in FIG. 7 indicate that the abrogation of suppression mediated by CD137L antibody in the "CD137$^{neg}$" culture is likely due to conversion of CD137$^{neg}$ to CD137$^{pos}$ cells when stimulated with anti-CD3/CD28 beads. This was demonstrated by showing that when cultured with CD3/CD28 beads, the CD137$^{neg}$ Tregs started to produce soluble CD137 protein (FIG. 8*b*), although the CD137$^{pos}$ Tregs produced significantly more (P=0.0001). Finally, CD137$^{pos}$ Tregs were still significantly more suppressive than CD137$^{neg}$ Tregs in the presence of the blocking antibody (P=0.006, FIG. 8*a*).

Figure 9:
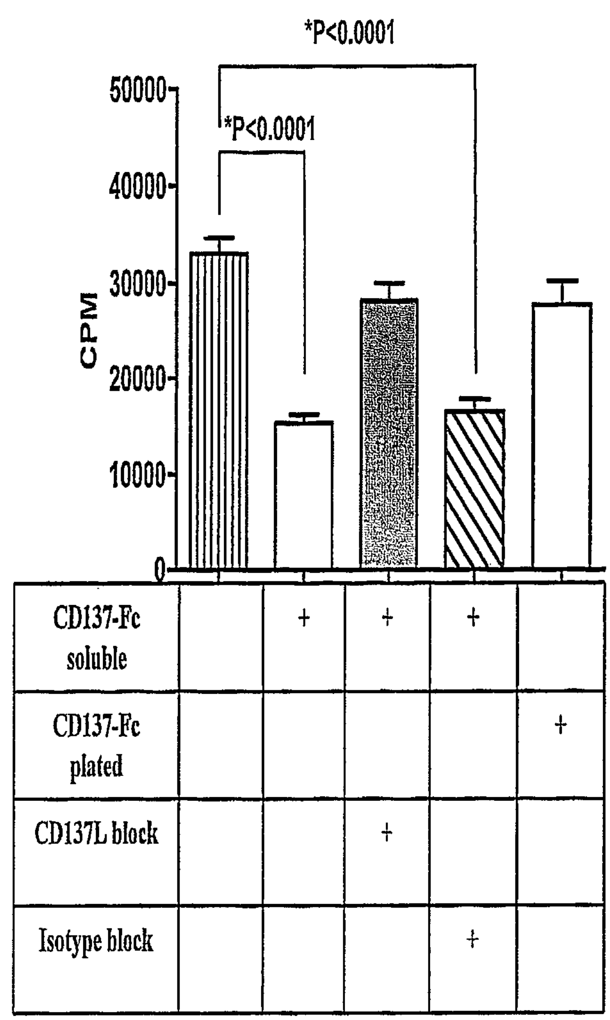
FIG. 9 shows that soluble CD137 directly suppresses T cells in an APC and Treg independent assay. NOD $CD4^{pos}CD25^{neg}CD137^{neg}$ T cells were sorted from 6-9 week old NOD female mice. 50,000 $CD4^{pos}CD25^{neg}CD137^{neg}$ T cells were cultured with 20,000 CD3/28 beads and 1 μg/ml of soluble CD137-Fc (n=6) or 2 μg/ml of plated CD137-Fc (n=6) in a 96 well U-bottom well. In the wells containing soluble CD137-Fc, 20 μg/ml of either CD137L blocking antibodies or isotype control antibodies (n=4) were added to some wells as indicated. All cells were plated in triplicate and pulsed with 1 μCi $^3$H/well on day 3 and harvested after 16 hours. Statistical analysis was performed using the unpaired t test.

The data demonstrate that soluble CD137 from CD137$^{pos}$ Tregs suppresses CD3/CD28 stimulated CD4$^{pos}$ T cells. Recombinant mouse CD137-Fc chimeric protein was used in a Treg-free assay. Culturing of CD4$^{pos}$CD25$^{neg}$CD137$^{neg}$ T cells with CD3/28 beads and either soluble or plate bound CD137-Fc chimera was performed (FIG. 9*a*). The addition of soluble CD137-Fc but not plate bound CD137-Fc significantly reduced the proliferation of CD3/CD28 stimulated CD4 T cells (P=0.0001), showing that soluble CD137-Fc can induce suppression of CD4$^{pos}$CD25$^{neg}$CD137$^{neg}$ T cells in vitro. To test whether this effect is mediated through CD137L, CD137L blocking or isotype control antibodies were added to the culture along with CD137-Fc (FIG. 9*a*). The addition of CD137L blocking antibody, but not the isotype control, abrogated the suppression mediated by CD137-Fc, confirming that CD137L is essential for suppression of CD4 T cells. The results demonstrate that the interaction of soluble CD137 with CD137L negatively regulates CD4 T cells.

Example 4

Figure 4:
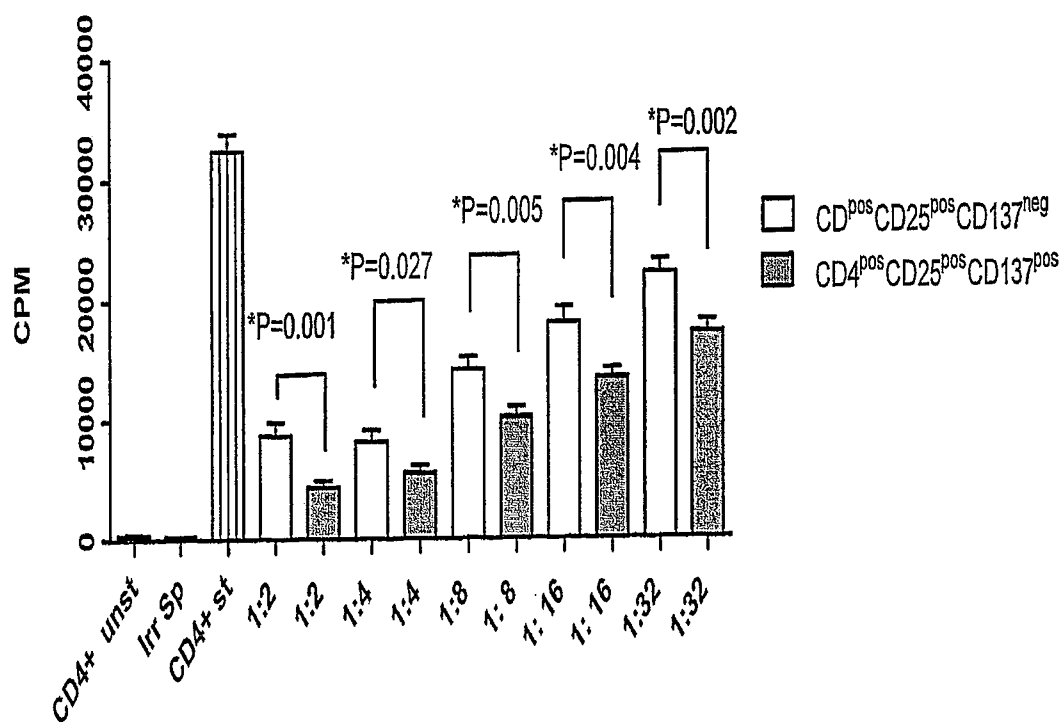
FIG. 4 shows NOD $CD137^{pos}$ Tregs are functionally superior to $CD137^{neg}$ Tregs in-vitro. Splenocytes from 4-11 week old NOD female mice were sorted for $CD4^{pos}CD25^{neg}CD137^{neg}$ T cells and $CD137^{neg}$ and $CD137^{pos}$ Tregs as described in Example 1. 50,000 $CD4^{pos}CD25^{neg}CD137^{neg}$ T cells were plated in U-bottom 96 well plate with 1.25 ug/well soluble anti-CD3, 50,000 irradiated (1500 rads) NOD splenocytes and 25,000 (1:2, n=10 experiments), 12,500 (1:4, n=7 experiments), 6250 (1:8, n=8 experiments), 3125 (1:16, n=8 experiments) and 1562 (1:32, n=7 experiments) $CD137^{neg}$ or $CD137^{pos}$ Tregs. The cells were pulsed with $^3$H labeled thymidine on day 3 and harvested after 16 hours. Statistical calculation was performed with the unpaired t test.

CD137 Expressing Tregs Mediate Contact Dependent and Contact Independent Suppression of T Cell Mediated Cell Death The results support enhanced CD137 mediated survival of CD137$^{pos}$ Tregs in NOD.B10 Idd9.3 mice. To understand the possible significance of increased percentage of CD137$^{pos}$ Tregs with age, investigation of the functional differences between CD137$^{neg}$ and CD137$^{pos}$ Treg subsets was performed. An in vitro suppression assay was performed using CD4$^{pos}$CD25$^{neg}$CD137$^{neg}$ T effector cells and titrated numbers of either CD137$^{pos}$ or CD137$^{neg}$ Tregs (FIG. 4*a*). The CD137$^{pos}$ Tregs are significantly functionally superior to CD137$^{neg}$ Tregs at every ratio (through 1:32, P=0.002) of Treg: T effector. This result shows that CD137-expressing Tregs are functionally superior and hence the decline in the number of these Tregs with age in NOD mice might be linked with decreased control of autoimmune effector cells.

Figure 5:
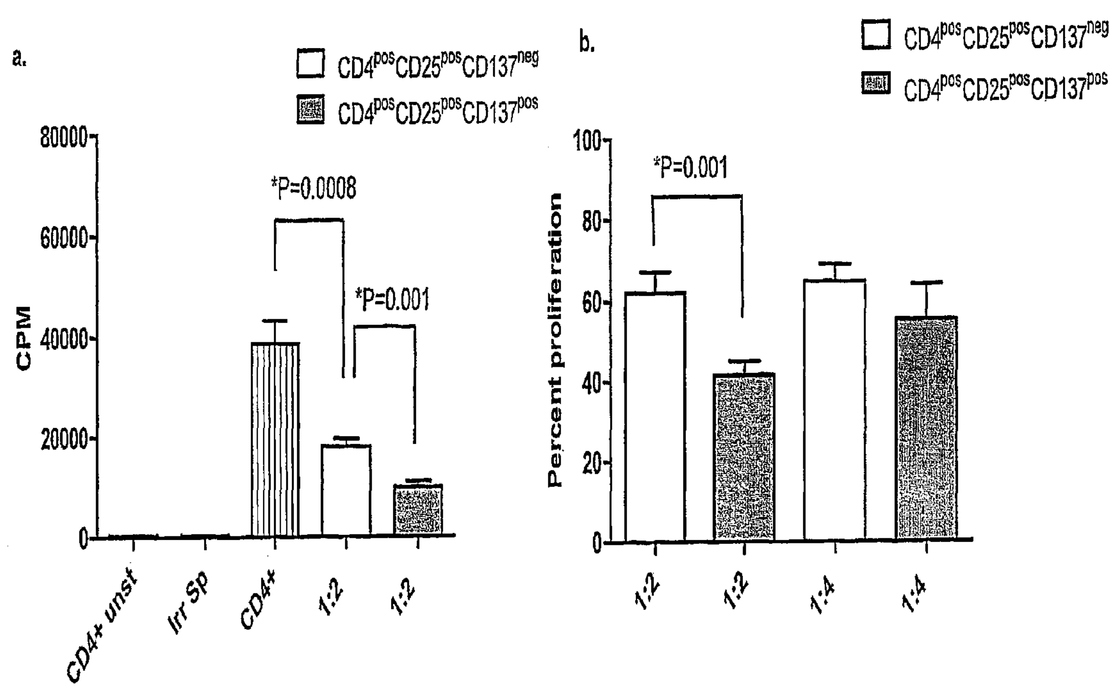
FIG. 5 shows $CD137^{pos}$ Tregs can suppress through contact independent mechanisms. (a) NOD $CD4^{pos}CD25^{neg}CD137^{neg}$ T cells and $CD137^{neg}$ and $CD137^{pos}$ Tregs were sorted from 5-9 week old mice. 100,000 $CD4^{pos}CD25^{neg}CD137^{neg}$ T cells were plated in the bottom of 96 well transwell plates with 1 μg/well soluble anti-CD3, and 50,000 $CD137^{neg}$ and $CD137^{pos}$ Tregs were cultured in the top wells. 100,000 irradiated (1500 Rads) splenocytes were added to the both the bottom and top transwells. The cells were pulsed with $^3$H-labeled thymidine on Day 3 and harvested after 16 hours. (b) Summary figure of transwell suppression assays performed at 1:2 (n=10) and 1:4 (n=3) ratios of Treg:T cell. The percentage proliferation was calculated by dividing the CPM counts of the wells with Tregs with the mean CPM count of the wells containing only $CD4^{pos}CD25^{neg}CD137^{neg}$ T cells. Statistical analysis was performed using the unpaired T test.

Next, CD137$^{pos}$ Tregs-mediated suppression through a contact-independent medium was studied. Transwell plated, and cultured CD4$^{pos}$CD25$^{neg}$CD137$^{neg}$ T cells were used in the bottom well with Treg subsets in the upper well. At a 1:2 ratio, both CD137$^{pos}$ and CD137$^{neg}$ Tregs can significantly suppress the proliferation of T cells, but CD137$^{pos}$ Tregs are significantly more suppressive than CD137$^{neg}$ Tregs (FIG. 5*a*). Ratios of Treg to effector above 1:2 did not show soluble suppression, consistent with a dilutional effect (supplemental FIG. 5*b*). This demonstrates that in a contact independent system, CD137$^{pos}$ Tregs can produce soluble factors that contribute to their functional superiority to CD137$^{neg}$ Tregs.

Example 5

Figure 2:
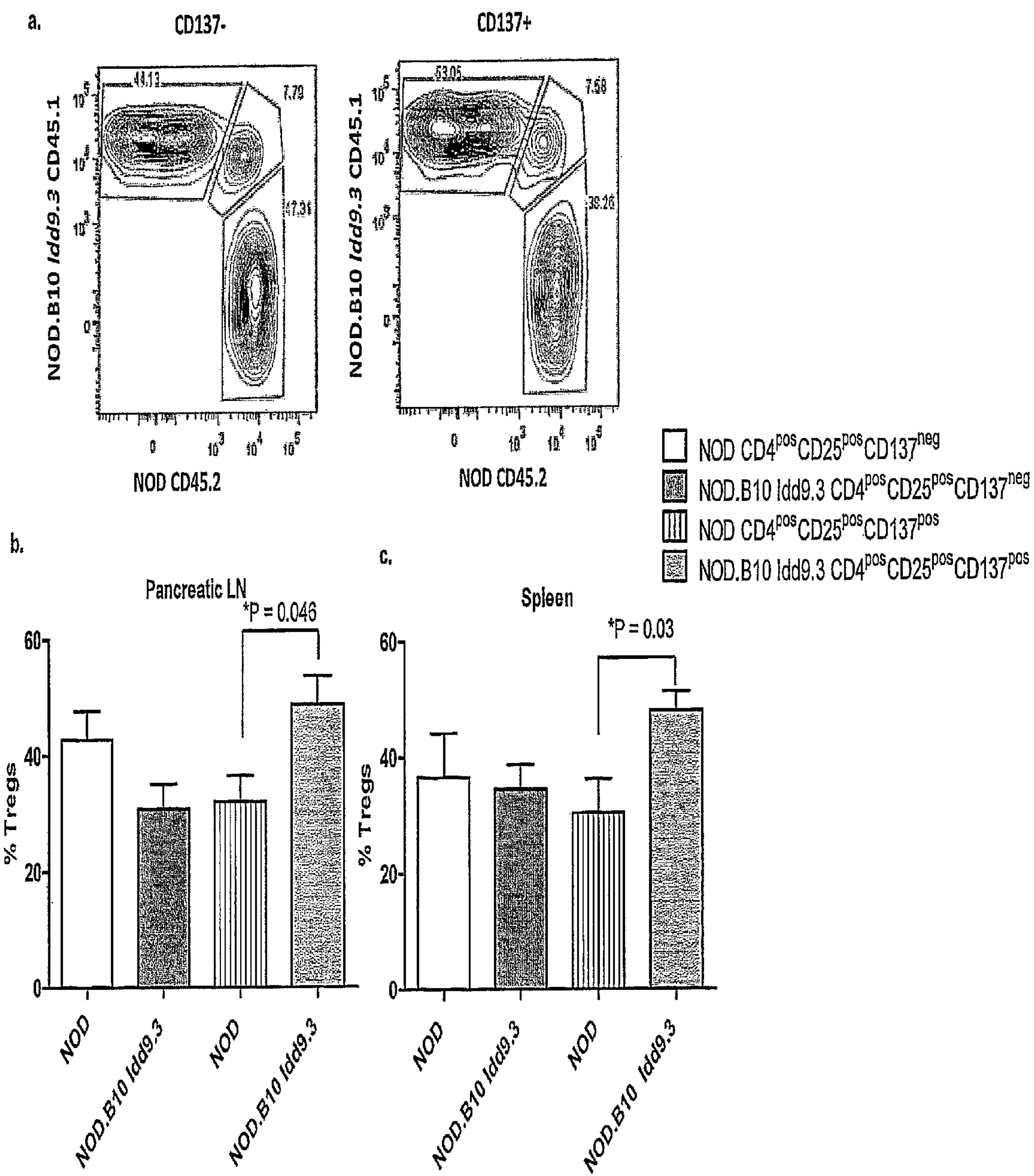
FIG. 2 shows mixed bone marrow chimeric studies demonstrate an intrinsic cell survival advantage of $CD137^{pos}$ Tregs expressing the B10 CD137 haplotype. 15-25 million bone marrow cells of 5-12 week old NOD.B10 Idd9.3 mice and NOD CD45.2 mice were mixed at 1:1 ratio and injected into 9-13 week old irradiated (NOD CD45.2×NOD.B10 Idd9.3) F1 mice. The recipient non-diabetic mice were sacrificed 12-20 week post injection. (a) One representative experiment showing the expression of the CD45.1 (NOD.B10 Idd9.3) vs. CD45.2 (NOD) allotype by $CD137^{neg}$ (left) and $CD137^{pos}$ (right) Tregs 12 weeks after reconstitution of the bone marrow chimera. (b) Spleen (n=5), and (c) pancreatic lymph nodes (n=4) were harvested and stained with CD4-APC-Cy7, CD25-Percp-Cy5.5, CD45.1-APC, CD45.2-FITC, and anti-CD137-PE and analyzed on a FACSCantos cytometer. Statistical significance was calculated using the unpaired t test.

Increased Expression of CD137$^{pos}$ Cells Enhances Long Term Survival of Tregs and the B12 CD137 Allele Mediates Enhanced Survival of CD137$^{pos}$ Tregs It has been demonstrated that agonist anti-CD137 treatment prevents diabetes in NOD mice, that a subset of Tregs constitutively expresses CD137, and that anti-CD137 binds to CD4$^{pos}$CD25$^{pos}$CD137$^{pos}$ Tregs in vitro and in vivo. The results showed that CD137$^{pos}$ Tregs may be important in T1D pathogenesis. Since CD137 is intimately associated with cell survival, investigation of changes in the frequency of CD137$^{pos}$ T regulatory cells with age in NOD and NOD.B10 Idd9.3 congenic mice was carried out. The frequency of CD137$^{pos}$ Tregs significantly declines with age in NOD, but not NOD.B10 Idd9.3 spleen (P=0.002, FIG. 1*a*). The percentage of CD137-expressing Tregs is significantly higher in older NOD B10 Idd9.3 than NOD spleen (P=0.0004, 21-36 week old) mice than in NOD mice (FIG. 2*a*). There is no statistically significant decline in the frequency of thymic (in contrast with peripheral) NOD CD137$^{pos}$ Tregs with age (FIG. 1*b*). However, the percentage of thymic NOD.B10 Idd9.3 CD137$^{pos}$ Tregs significantly increased with age, and is significantly higher in 21-36 week old NOD.B10 Idd9.3 mice versus NOD mice (P=0.01, FIG. 1*b*).

In order to investigate the reason for increased NOD.B10 Idd9.3 CD137pos Treg survival with age, the examination of the cell-surface expression of CD137 at the same time points was carried out. The mean florescence intensity of CD137 in CD4posCD25posCD137pos T cells was significantly greater in young (3-9 week old) NOD.B10 Idd9.3 versus NOD splenic and thymic CD137pos Tregs (P=0.0009 and P=0.0003 respectively, FIG. 1*c, d*). Although the percentage of CD4posCD25posCD137pos T cells declined markedly in 21-36 week old NOD spleen, the cells that survived expressed a higher level of CD137 on a per cell basis, comparable to the surviving NOD.B10 Idd9.3 Tregs. (FIG. 1*a, c*). These findings show that early, increased expression of CD137 on Tregs enhances long term survival of those cells. This is supported by the finding that the mean expression of CD137 is high on all surviving CD137 Tregs in both NOD and NOD B10 mice. NOD.B10 Idd9.3 congenic CD137pos Tregs had more CD137 on a per cell basis in both spleen and thymus than NOD Tregs, associated with a lack of age related decline in the percentage of CD4posCD25posCD137pos T cells.

These results demonstrate that the decline in the number of CD137$^{pos}$ Tregs could be due to reduced survival of these cells. Viability studies in CD137 stimulated and unstimulated T cells have shown that CD137 signaling prevents activation induced cell death (AICD) by preventing DNA fragmentation. CD137 co-stimulation causes proliferation of Tregs in vitro and in vivo. This evidence indicates that CD137 co-stimulation is important for the survival of Tregs. To test whether the NOD B10 Cd137 haplotype intrinsically mediated increased survival in CD137$^{pos}$ Tregs, construction of mixed bone marrow chimeras using NOD and NOD.B10 Idd9.3 CD137$^{pos}$ bone marrow transferred into (NOD.CD45.2×NOD.B10 Idd9.3 (CD45.1)) F1 mice was performed. The resulting chimeric mice were analyzed for effective reconstitution and relative ratios of allotypically marked cells as shown in FIG. 2*a*. In the mixed bone marrow chimera mice, the percentage of peripheral (splenic or pancreatic lymph node) CD4$^{pos}$CD25$^{pos}$CD137$^{pos}$ T cells expressing the NOD.B10 Idd9.3 CD137 haplotype was significantly increased compared to CD137$^{pos}$ Tregs with the NOD haplotype (FIG. 2*b, c*). CD137$^{neg}$ Tregs, in contrast, show no significant CD45.1 vs. CD45.2 population differences (FIG. 2*a-c*). There was no statistically significant difference in thymic CD45.1 vs. CD45.2 proportions (not shown). These results show that the B10 CD137 allele intrinsically mediates enhanced survival of CD137$^{pos}$ Tregs.

Example 6

Figure 3:
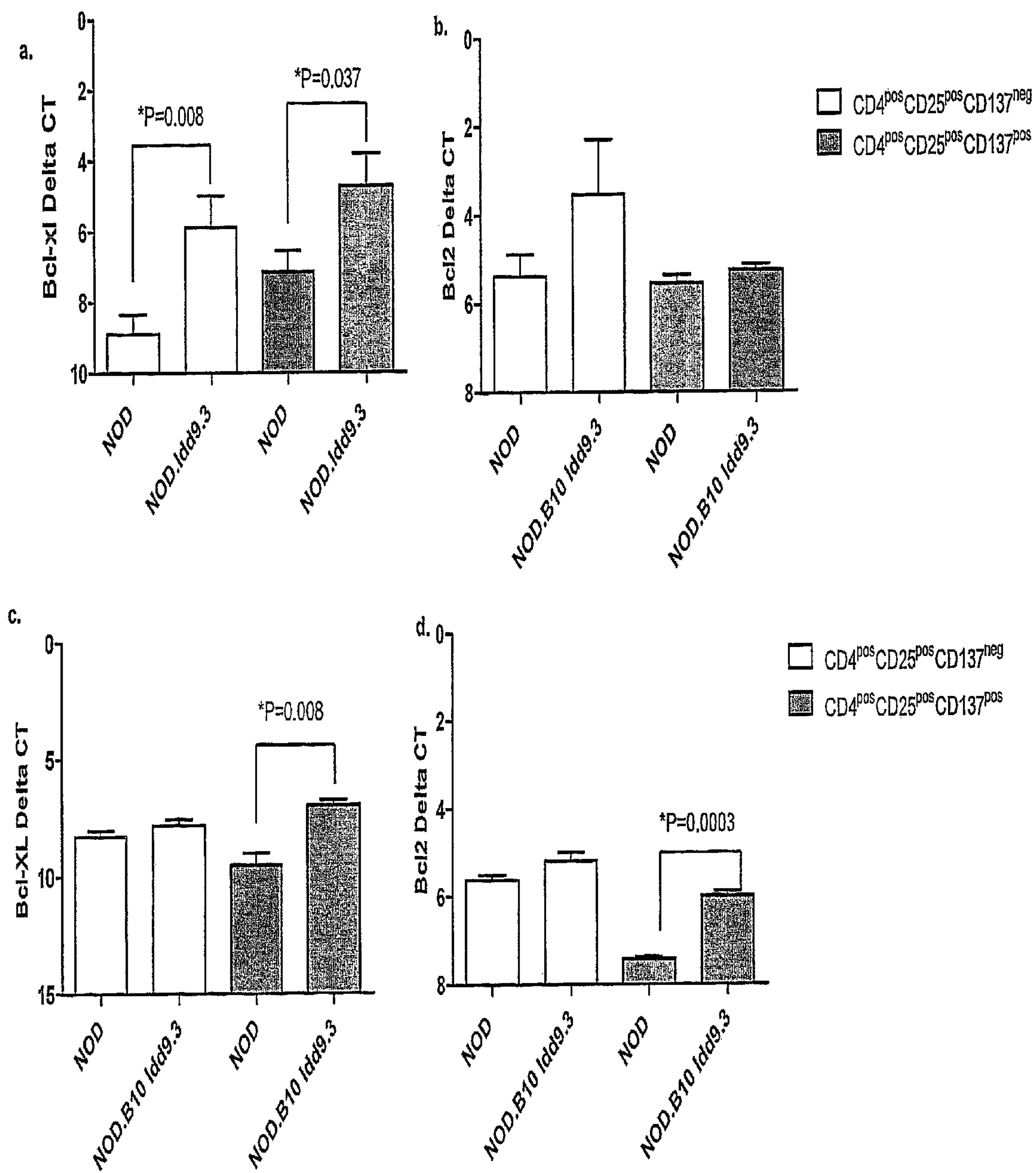
FIG. 3 shows NOD.B10 Idd9.3 $CD137^{pos}$ Tregs express higher levels of Bcl-xl and Bcl2, than NOD $CD137^{pos}$ Tregs in NOD vs. NOD.B10 Idd9.3 mice and in mixed bone marrow chimeras. (a) Splenocytes from 4-7 week old NOD (n=9) and NOD.B10 Idd9.3 (n=6) females were used for sorting up to 50,000 $CD4^{pos}CD25^{neg}CD137^{neg}$, $CD4^{pos}CD25^{pos}CD137^{neg}$, and $CD4^{pos}CD25^{pos}CD137^{pos}$ cells. RNA was extracted from the sorted cells and converted to cDNA as described in the methods. Quantitative Real Time Polymerase Chain Reaction (RTPCR) was performed on the cDNA using B2m or Gapdh and Bcl-xl primers (Applied Bioscience) (b) 4-7 week old NOD (n=3) and NOD.B10 Idd9.3 (n=3) female splenocytes were used for sorting 50,000 $CD4^{pos}CD25^{neg}CD137^{neg}$, $CD4^{pos}CD25^{pos}CD137^{neg}$, and $CD4^{pos}CD25^{pos}CD137^{pos}$ cells and used for RT-PCR with B2m and Bcl2 primers. (c, d) 15 million bone marrow cells of 10-11 week old NOD.B10 Idd9.3 mice and NOD.CD45.2 mice were mixed at 1:1 ratio and injected into 16 week old irradiated (NOD.CD45.2×NOD.B10 Idd9.3) F1 mice (see methods). Recipient non-diabetic mice were sacrificed 9-10 week post injection. $CD137^{neg}$ and $CD137^{pos}$ Tregs were sorted according to CD45.1 (NOD.B10 Idd9.3) vs CD45.2 (NOD) allotype in F1 recipients and used for RT-PCR with B2m and Bcl-xl (c) or Bcl2 (d) primers (n=3 each). Statistical calculation was performed using the unpaired t test.

B10 CD137 Allele Mediates Enhanced Expression of the Pro-Survival Molecule Bcl-xl The expression of Bcl-xl in NOD vs. NOD.B10 Tregs was tested in NOD and NOD.B10 Idd9.3 mice and in the mixed bone marrow chimeras. Significantly increased expression of Bcl-xl in NOD.B10 Idd9.3 versus NOD CD137$^{pos}$ Tregs was observed, consistent with survival results (P=0.037, FIG. 3*a*). Of interest, increased expression of Bcl-xl in NOD.B10 Idd9.3 versus NOD CD137$^{neg}$ Tregs was noted. In contrast, there were no differences in Bcl2 expression in the same cell subsets (FIG. 3*b*). In the mixed bone marrow chimera experiments, CD137$^{pos}$, but not CD137$^{neg}$ Tregs expressing the NOD.B10 vs. NOD CD137 haplotype expressed significantly increased Bcl-xl, consistent with the finding of increased survival in these cells (P=0.008, FIG. 3*c*). In the chimeric mice, as opposed to unmanipulated mice, CD137$^{pos}$ cells expressing the B10 CD137 haplotype also showed increased Bcl2 compared with cells expressing the NOD haplotype (FIG. 3*d*). This shows that the B10 Cd137 allele enhances a pro-survival signal leading to increased CD137$^{pos}$ peripheral Tregs survival.

Example 7

CD4$^{pos}$CD25$^{pos}$ T Cells are Essential for Anti-CD137 Mediated Diabetes Prevention To show that CD4$^{pos}$CD25$^{pos}$ Tregs are essential for anti-CD137 mediated disease protection, NOD mice were pre-treated with anti-CD25 antibody that depleted CD4$^{pos}$CD25$^{pos}$ T cells (as confirmed by FACS). CD25 depletion was followed by three doses of anti-CD137 injection at one-week intervals. Control mice were treated with anti-CD25 alone or PBS.

Seven week old NOD female mice were treated with 330 ug of anti-CD25 antibody or PBS twice at a one week interval. One day after the second injection, the mice were either untreated or treated three times with 200 μg of anti-CD137 (clone 3H3) at 3-week intervals. The groups consisted of: CD25 alone (n=11), 3H3 alone (n=9), PBS alone (n=7), and both CD25 and 3H3 (n=11). The mice were tested for glucososuria weekly. The P value was calculated using the logrank statistic in Graphpad.

Figure 10:
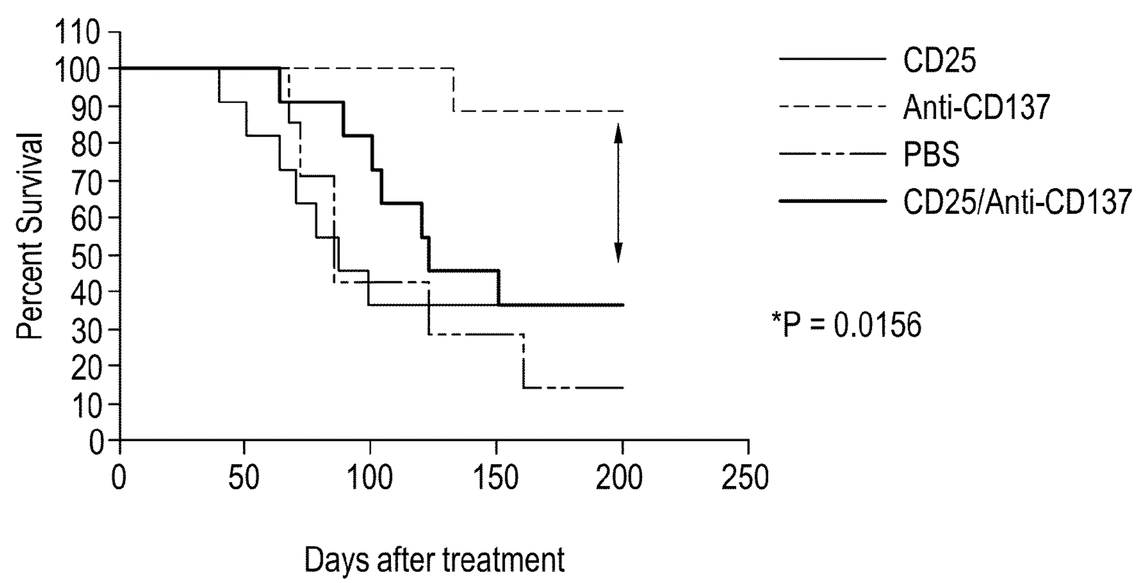
FIG. 10 shows that $CD4^{pos}CD25^{pos}$ T cells are essential for anti-CD137 mediated diabetes prevention. Seven week old NOD female mice were treated with 330 μg of anti-CD25 antibody or PBS twice at a one week interval. One day after the second injection, the mice were either untreated or treated three times with 200 μg of anti-CD137 (clone 3H3) at 3-week intervals. The groups consisted of: CD25 alone (n=11), 3H3 alone (n=9), PBS alone (n=7), and both CD25 and 3H3 (n=11). The mice were tested for glucososuria weekly. The P value was calculated using the logrank statistic in Graphpad.

Mice that were treated with anti-CD137 antibody were significantly protected from diabetes (FIG. 10). Mice that were pre-treated with anti-CD25 antibody prior to anti-CD137 treatment, however, showed no protection from diabetes (FIG. 10), demonstrating that the presence of CD25$^{pos}$ Tregs at the time of anti-CD137 treatment was necessary for its protective effect. The anti-CD25/anti-CD137, anti-CD25 alone and PBS treated mice all succumbed to diabetes within 50-150 days after treatment and these treatments showed no significant differences; notably treatment with anti-CD25 alone did not exacerbate onset of diabetes (FIG. 10). This result confirms that $CD4^{pos}CD25^{pos}$ T cells are indispensable for preventing diabetes with anti-CD137 therapy in NOD mice. Results indicate that $CD137^{pos}$ Tregs, targeted by anti-CD137 antibody is important in diabetes pathogenesis.

Example 8

Anti-CD137 Treatment Induces a Signaling Response in $CD4^{pos}CD25^{pos}CD137^{pos}$ T Cells In Vivo CD137 belongs to TNFR superfamily of receptors that bind to TNFR-associated factors (TRAFs) intracellularly. TRAF1/2 has been shown to be upregulated by CD137 stimulation in T cells. In order to show that anti-CD137 antibody causes downstream signaling of CD137 in Tregs, NOD mice were treated with anti-CD137 antibody and after 24 hours isolated $CD4^{pos}CD25^{neg}CD137^{neg}$, $CD4^{pos}CD25^{pos}CD137^{neg}$, and $CD4^{pos}CD25^{pos}CD137^{pos}$ T cells by cell sorting.

Figure 11:
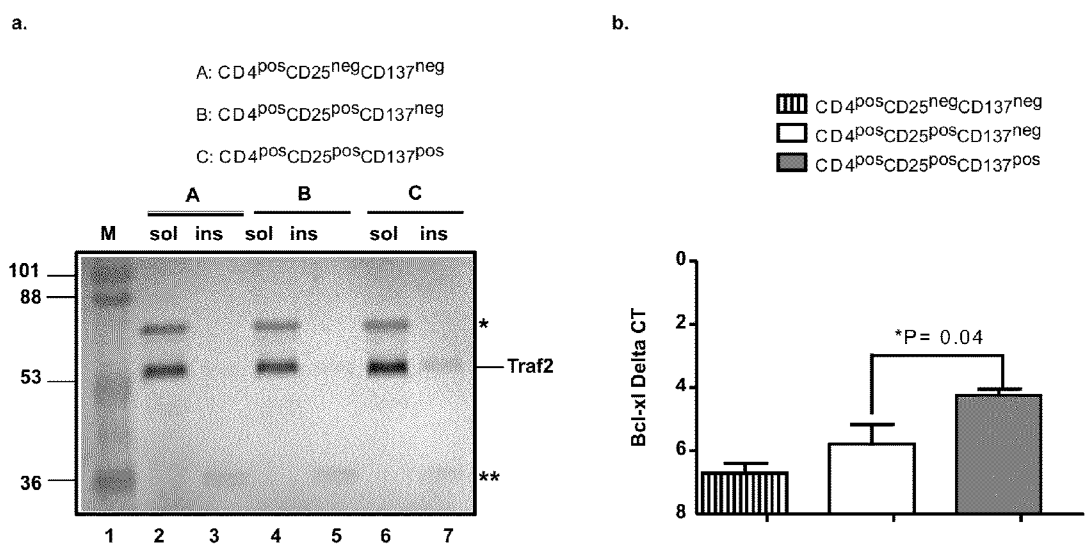
FIG. 11 shows that $CD137^{pos}$ Tregs from anti-CD137 treated NOD mice redistribute TRAF2 to the cell surface and express higher levels of Bcl-xl mRNA. NOD mice (n=2) were treated with 200 μg of anti-CD137 once and $CD4^{pos}CD25^{neg}CD137^{neg}$, $CD4^{pos}CD25^{pos}CD137^{neg}$, and $CD4^{pos}CD25^{pos}CD137^{pos}$ T cells were sorted after 24 hrs. (a) Western blot of lysate proteins (after 10% SDS-PAGE) show redistribution of 55 kDa TRAF2 protein from soluble (i.e., cytoplasm) to insoluble (i.e., membrane-bound) fractions following stimulation with antibody in vivo. Starred bands represent either residual fetal bovine serum (*) from the media or an unidentified, membrane-bound mouse phosphatase (**), which reacts with the BCIP/NBT substrate. Lane 1 contains pre-stained protein size markers (kDa). (b) 13-14 week old NOD females were treated with 200 μg of anti-CD137 twice for two weeks. One day after the second treatment, the mice were sacrificed and sorted into $CD4^{pos}CD25^{neg}CD137^{neg}$, $CD4^{pos}CD25^{pos}CD137^{neg}$, and $CD4^{pos}CD25^{pos}CD137^{pos}$ T cells with CD4APC, CD25FITC, anti-IgG2a biotin and Streptavidin-PE antibodies. RNA was extracted from the sorted cells and converted into cDNA. RT-PCR was performed using GAPDH and Bcl-xl primers (n=6). Statistical calculations were performed using the unpaired t test.

NOD mice (n=2) were treated with 200 ug of anti-CD137 once and $CD4^{pos}CD25^{neg}CD137^{neg}$, $CD4^{pos}CD25^{pos}CD137^{neg}$, and $CD4^{pos}CD25^{pos}CD137^{pos}$ T cells were sorted after 24 hrs. Western blot of lysate proteins (after 10% SDS-PAGE) show redistribution of 55 kDa TRAF2 protein from soluble (i.e., cytoplasm) to insoluble (i.e., membrane-bound) fractions following stimulation with antibody in vivo. Starred bands represent either residual fetal bovine serum (*) from the media or an unidentified, membrane-bound mouse phosphatase (), which reacts with the BCIP/NBT substrate. Lane 1 contains pre-stained protein size markers (kDa) (See FIG. 11***a*). 13-14 week old NOD females were treated with 200 ug of anti-CD137 twice for two weeks. One day after the second treatment, the mice were sacrificed and sorted into $CD4^{pos}CD25^{neg}CD137^{neg}$, $CD4^{pos}CD25^{pos}CD137^{neg}$ and $CD4^{pos}CD25^{pos}CD137^{pos}$ T cells with CD4APC, CD25FITC, anti-IgG2a biotin and StrepavidinPE antibodies. RNA was extracted from the sorted cells and converted into cDNA. RT-PCR was performed using GAPDH and Bcl-xl primers (n=6). Statistical calculations were performed with unpaired t test. (See FIG. 11*b*)

TRAF2 western blot analysis performed under reducing conditions was used to look for redistribution of the TRAF2 protein from the cytoplasm (i.e., soluble) to the cell surface (i.e., insoluble) fractions. The results show that 55 kDa TRAF2 migrates from the cytoplasm to the cell surface in $CD4^{pos}CD25^{pos}$ T cells that binds to CD137 antibody in vivo (after treatment) but not in $CD4^{pos}CD25^{neg}CD137^{neg}$ or $CD4^{pos}CD25^{pos}CD137^{neg}$ T cells (FIG. 11*a*). These results indicate that anti-CD137 antibody treatment specifically targets $CD137^{pos}$ Tregs in vivo and initiates downstream signaling in these cells. Studies have shown that CD137 co-stimulation in T cells leads to upregulation of pro-survival molecule Bcl-xl downstream signaling pathway. Bcl-xl mRNA levels were tested in the treated T cells subsets. As expected, $CD4^{pos}CD25^{pos}$ T cells that bound to CD137 in vivo (in antibody treated mice) expressed significantly higher levels of Bcl-xl than $CD4^{pos}CD25^{neg}CD137^{neg}$ or $CD4^{pos}CD25^{pos}CD137^{neg}$ T cells (See FIG. 11*b*). Results confirm that anti-CD137 antibody specifically targets $CD4^{pos}CD25^{pos}CD137^{neg}$ T cells and initiates downstream signaling through Traf2 and Bcl-xl.

Example 9

Anti-CD137 Treatment Does not Alter Foxp3, IL-10, or TFG-β in $CD137^{pos}$ Tregs Since anti-CD137 treatment specifically targets CD137 expressing $CD4^{pos}CD25^{pos}$ T cells, other Treg markers that are affected by the antibody treatment were tested, including Foxp3, IL-10, and TGF-β.

Figure 12:
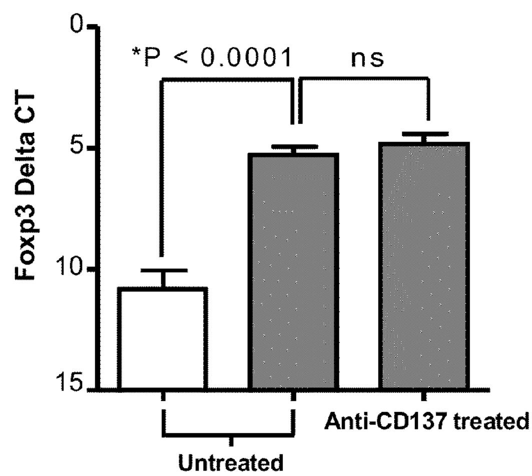
FIG. 12 shows that anti-CD137 treatment does not alter Foxp3, IL-10, or TGF-β levels on $CD137^{pos}$ Tregs. The splenocytes from 4-12 week old NOD females were treated with 200 μg of anti-CD137 twice for two weeks. One day after the second treatment, the mice were sacrificed and were stained with CD4-APC, CD25-FITC, anti-IgG2a, and Streptavidin-PE. 4-12 week old untreated NOD females were also stained with CD4-APC, CD25-FITC, and CD137PE. 15,000 $CD4^{pos}CD25^{neg}CD137^{neg}$ and $CD4^{pos}CD25^{pos}CD137^{pos}$ T cells were FACS sorted from both treated and untreated mice. RNA was extracted from the sorted cells and converted to cDNA. Quantitative Real Time Polymerase Chain Reaction (RTPCR) was performed on the cDNA using GAPDH and (a) Foxp3 (n=8 untreated, n=5 treated), (b) IL-10 (n=6 untreated, n=5 treated) and (c) TGF-β (n=6 untreated, n=6 treated) primers. Statistical calculations were performed using the unpaired t test.
Figure 12:
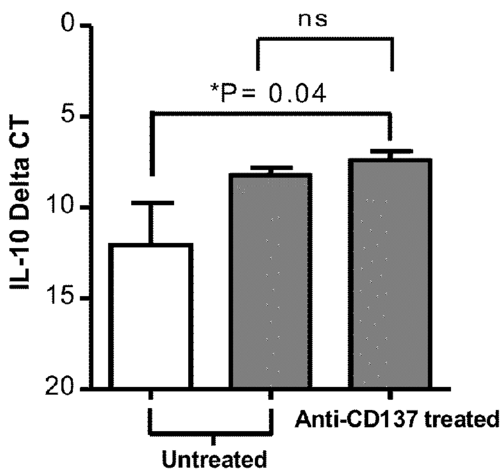
Figure 12:
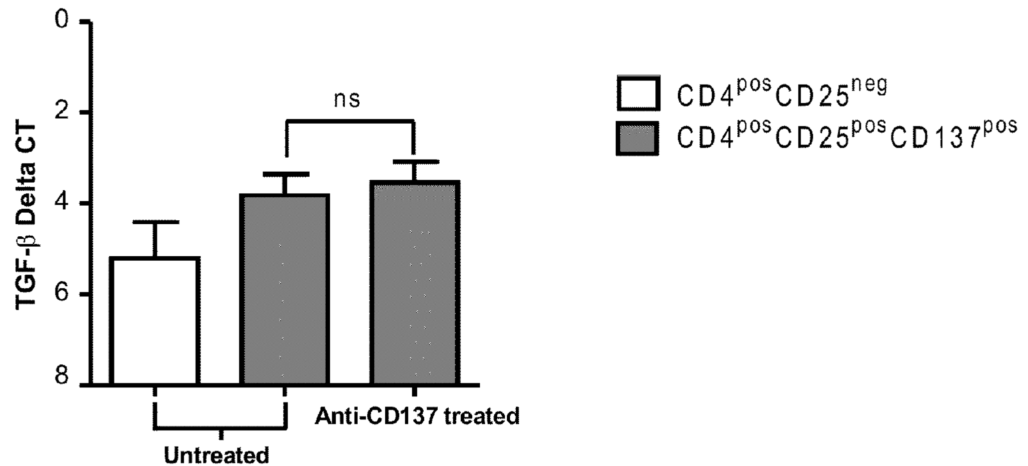

The splenocytes from 4-12 week old NOD females were treated with 200 ug of anti-CD137 twice for two weeks. One day after the second treatment, the mice were sacrificed and were stained with CD4-APC, CD25-FITC, anti-IgG2a and Streptavidin-PE. 4-12 week old untreated NOD females were also stained with CD4-APC, CD25-FITC, and CD137PE. 15,000 $CD4^{pos}CD25^{neg}CD137^{neg}$ and $CD4^{pos}CD25^{pos}CD137^{pos}$ T cells were FACS sorted from both treated and untreated mice. RNA was extracted from the sorted cells and converted to cDNA as described in Example 1. Quantitative Real Time Polymerase Chain Reaction (RT-PCR) was performed on the cDNA using GAPDH and (a) Foxp3 (n=8 untreated, n=5 treated), (b) IL-10 (n=6 untreated, n=5 treated) and (c) TGF-β (n=6 untreated, n=6 treated) primers. Statistical calculations were performed with unpaired t test Results show that anti-CD137 treatment does not alter the Foxp3 mRNA levels in $CD137^{pos}$ Tregs but is significantly higher than $CD4^{pos}CD25^{neg}$ T cells (FIG. 12*a*). Results also support the conclusion that $CD137^{pos}$ Tregs from untreated mice produce high levels of Foxp3 protein. Results further show that anti-CD137 treatment does not alter the IL-10 mRNA levels between treated and untreated $CD137^{pos}$ Tregs, but treated Tregs express significantly higher levels of IL-10 mRNA than $CD4^{pos}CD25^{neg}$ T cells (FIG. 12*b*, P=0.04). Results suggest that $CD137^{pos}$ Tregs may contribute to some of the increased IL-10 production after anti-CD137 treatment. Anti-CD137 treatment also does not alter TGF-β mRNA levels in $CD137^{pos}$ Tregs (FIG. 12*c*). These results showed that anti-CD137 antibody does not change Foxp3, IL-10 or TGF-13 production in $CD137^{pos}$ Tregs.

Example 10

Anti-CD137 Treatment to NOD Enhances Soluble CD137 Production from $CD137^{pos}$ Tregs In Vitro NOD $CD137^{pos}$ Tregs produce high levels of soluble CD137 in vitro upon IL-2 stimulation. Here, whether anti-CD137 treatment alters soluble CD137 production from $CD137^{pos}$ Tregs was investigated.

Figure 13:
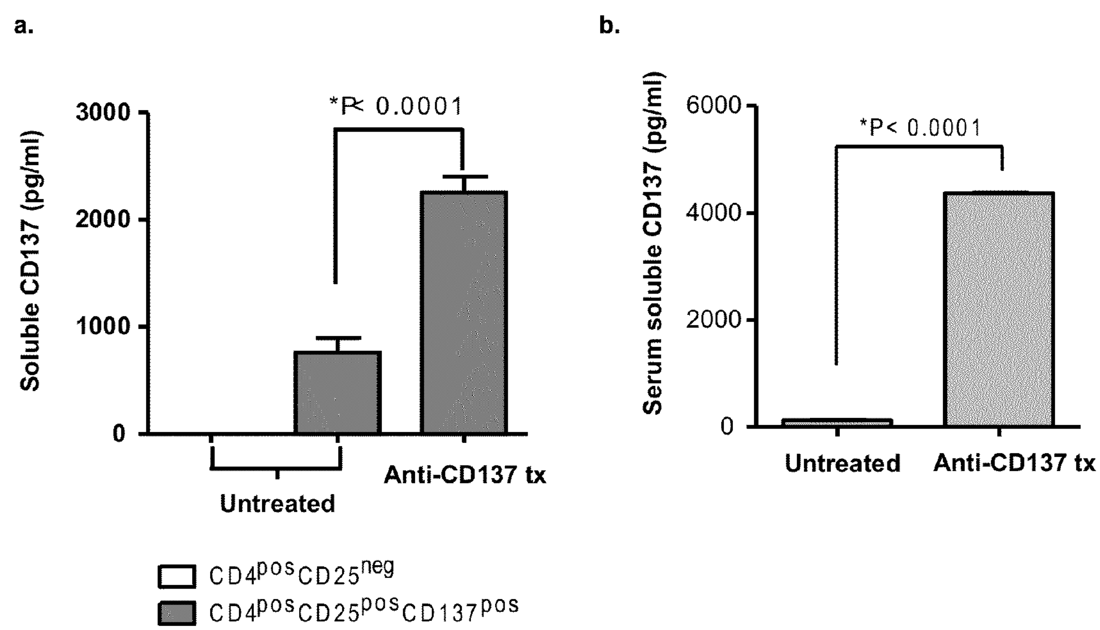
FIG. 13 shows that $CD137^{pos}$ Tregs from anti-CD137 treated mice produce highest levels of soluble CD137 ex vivo and anti-CD137 treatment increases soluble CD137 production in NOD mice. (a) NOD mice (n=2) were treated with 100 μg of anti-CD137 antibody or left untreated (n=2). In untreated mice, $CD4^{pos}CD25^{neg}CD137^{neg}$ and $CD4^{pos}CD25^{pos}CD137^{pos}$ T cells were sorted; the same cells were sorted using IgG2a secondary antibody and streptavidin. The cells were cultured in 96-well U-bottom plate with 25 U/ml IL-2 for 5 days. ELISA was performed on their supernatants for soluble CD137 (n=2 experiments). (b) NOD mice (n=3) were treated with 100 μg of anti-CD137 antibody or left untreated (n=8). The mice were sacrificed after 24 hrs and their serum was tested for soluble CD137 with ELISA. Statistical analysis was performed using the unpaired t test.

NOD mice (n=2) were treated with 100 ug of anti-CD137 antibody or left untreated (n=2) (FIG. 13*a*). In untreated mice, $CD4^{pos}CD25^{neg}CD137^{neg}$ and $CD4^{pos}CD25^{pos}CD137^{pos}$ T cells were sorted as mentioned above and in treated mice; the same cells were sorted using IgG2a secondary antibody and streptavidin. The cells were cultured in 96-well U-bottom plate with 25 U/ml IL-2 for 5 days. ELISA was performed on their supernatants for soluble CD137 (n=2 experiments). NOD mice (n=3) were treated with 100 ug of anti-CD137 antibody or left untreated (n=8) (FIG. 13*b*). The mice were sacrificed after 24 hrs and their serum was tested for soluble CD137 with ELISA as described in the methods section. The statistical analysis was performed using unpaired t test.

Results indicate that Tregs bound to anti-CD137 antibody in vivo produced high levels of soluble CD137. $CD4^{pos}CD25^{neg}$ T cells from untreated mice did not produce any soluble CD137 under these in vitro conditions.

Soluble CD137 is increased in the serum of patients with rheumatoid arthritis and systemic lupus (Jung, H. W. et al., Serum concentrations of soluble 4-1BB and 4-1BB ligand correlated with the disease severity in rheumatoid arthritis, Exp. Mol. Med. 36(1): 13-22 (2004)). Since CD137$^{pos}$ Tregs subsets produce high levels of soluble CD137 after treatment, serum soluble CD137 levels were analyzed. NOD mice were treated with two doses of either anti-CD137 antibody or PBS control, 8 days and 24 hrs prior to sacrifice. The serum was collected and tested for soluble CD137 with ELISA. Anti-CD137 treatment caused a dramatic increase in soluble CD137 levels in NOD serum compared to the untreated control (FIG. 13*b*).

Example 11

Treg Produced Soluble CD137 Directly Suppresses CD4$^{pos}$ T Effector Cells Via Interacting with CD137L CD137$^{pos}$ Tregs are the greatest producers of soluble CD137 in vitro. The production of soluble CD137 has been associated with decreased T cell proliferation, and increased cell death and DNA fragmentation. Here, CD137$^{pos}$ Tregs suppression through soluble CD137 in a contact independent in vitro system was assessed. CD137$^{pos}$ Tregs can suppress at 1:2 Treg to T effectors ratio in a transwell system. It has also already been shown that soluble CD137 binds to CD137L in vitro. Here, CD137L blocking antibody was used to obstruct soluble CD137 mediated suppression of CD4 T cells in a transwell system. To eliminate any complexities associated with the expression of CD137L on splenic macrophages or dendritic cells, anti-CD3/CD28 coated beads were used for stimulation instead of APC.

NOD CD4$^{pos}$CD25$^{neg}$CD137$^{neg}$ and CD4$^{pos}$CDP$^{pos}$CD137$^{pos}$ T cells were sorted from 5-7 week old NOD mice. 100,000 CD4$^{pos}$CD25$^{neg}$CD137$^{neg}$ T cells were plated in the bottom of a 96 well transwell plate with 50,000 CD4$^{pos}$CD25$^{pos}$CD137$^{pos}$ T cells in the top well. 50,000 CD3/CD28 beads were added to the bottom and to the top of the plate. 20 ug/ml of CD137 ligand blocking antibody (n=4 experiments) or IgG2a isotype antibody (n=3 experiments) were added to the bottom wells. The cells were pulsed with 3H labeled thymidine on day 3 and harvested after 16 hours. Statistical analysis was performed using unpaired t test.

CD137L blocking was employed on CD4$^{pos}$CD25$^{neg}$CD137$^{neg}$ T cells to assess the role of CD137-CD137L co-stimulation in the proliferation of CD4 T cells. CD137L blocking did not alter the proliferation of CD4$^{pos}$CD25$^{neg}$CD137$^{neg}$ T cells, indicating that CD137L blocking antibody does not act to abrogate proliferation by interrupting CD137-CD137L interactions between CD4$^{pos}$ effector T cells (FIG. 14). However, the presence of CD137L blocking antibody significantly abrogated suppression of CD137$^{pos}$ Tregs (P=0.001), while the isotype antibody had no effect on suppression (FIG. 14). Results indicate that soluble CD137 produced by CD137$^{pos}$ Tregs suppressed the proliferation of CD4 effector T cells. This result is consistent the observation that CD137$^{pos}$ Tregs produce high levels of soluble CD137 in a contact-dependent APC-independent suppression assay. Hence, the CD137L antibody must act to block the effect of soluble CD137 on the CD4$^{pos}$ effector T cells. Therefore soluble CD137 actively suppressed CD4$^{pos}$ T cell proliferation in vitro. Results show that CD137$^{pos}$ Tregs can mediate superior suppression through soluble CD137 in a contact independent system.

Example 12

Figure 15:
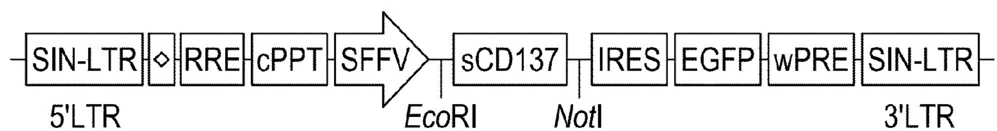
FIG. 15 shows that lentivirally-transduced HEK293 cells produce recombinant soluble CD137 protein in vitro. (a) shows a schematic of the lentiviral vector, LeGO-iG2-sCD137, used to express soluble protein. The wild type (B6) mouse sCD137 cDNA was inserted between the unique restriction sites EcoRI and NotI. The soluble CD137 minigene is expressed from the strong SFFV promoter with a downstream EGFP reporter used to label cells that the viral vector has incorporated. (b) $0.5\times10^6$ NIH3T3 cells, either un-transfected (thin solid line), un-sorted (even dashed line), sorted on medium expression of EGFP (uneven dashed line), or sorted on high expression of EGFP (thick solid line) were identified using a four-laser FACSAria II. Recovered cells were cultured in IMDM for 3 weeks after the original sort and stable EGFP expression assessed by FACSCalibur. (c) Mouse NIH3T3 fibroblasts and human embryonic kidney (HEK293) cells were transduced with lentiviral particles LeGO-iG2-sCD137. The transduced NIH3T3 and HEK293 cells exhibiting stable EGFP expression were sorted for high (top 10%) and medium (middle 40-70%) EGFP expression using FACS Arial II flow cytometry. The sorted cell lines were subsequently re-plated and cultured for an additional five days in IMDM with 10% FBS before checking soluble CD137 expression by ELISA.
Figure 15:
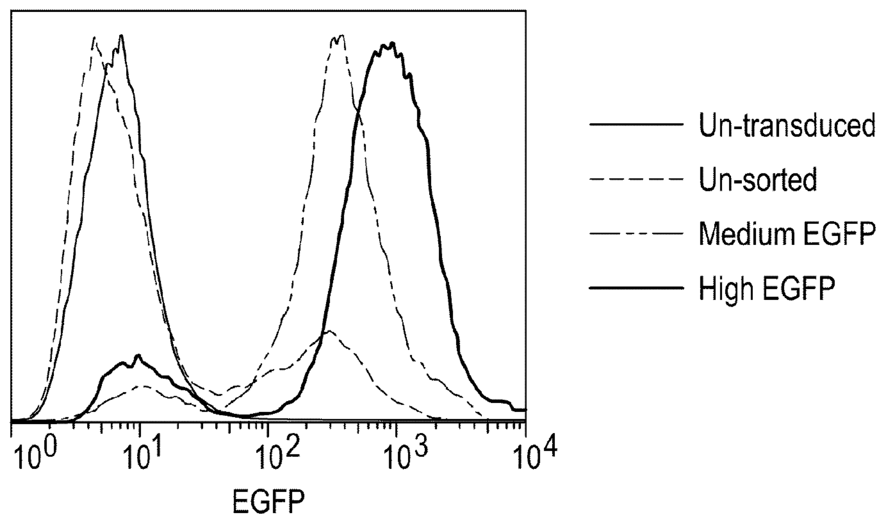
Figure 15:
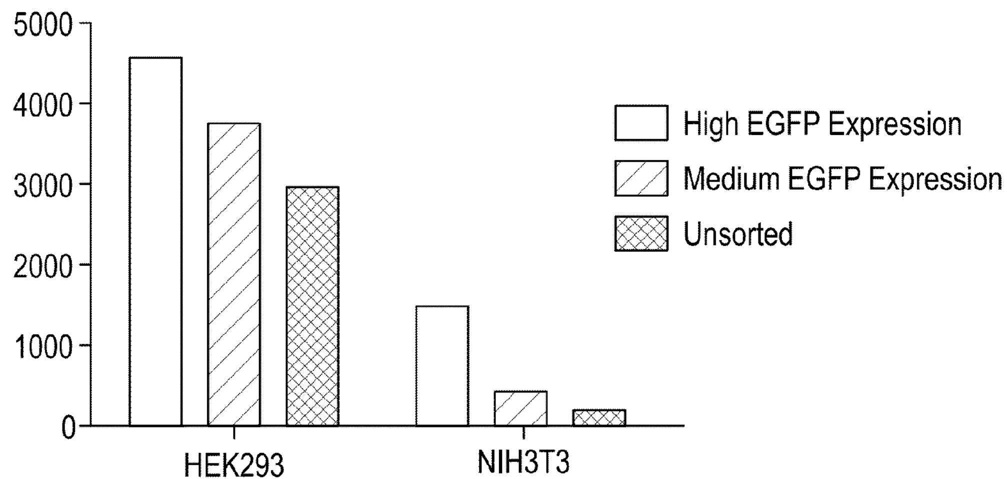

Lentivirally-Transduced HEK293 Cells Produce Recombinant Soluble CD137 Protein In Vitro Since anti-CD137 treatment of mice increases soluble CD137 production in vivo, the next step involved assessing whether purified soluble CD137 may have an effect on T1D progression in NOD mice. To accomplish this, a soluble CD137 minigene was subcloned into the lentiviral vector, LeGO-iG2 (FIG. 15*a*). The LeGO-iG2 expression vector has EGFP downstream of CD137 insert, which detects soluble CD137 production and a highly active promoter, the spleen focus forming viral (SFFV) which allows for the protein to be produced in high enough amounts. The LeGO-iG2 vector is self-inactivating (SIN) Lentiviral Gene Ontology (LeGO)-based bicistronic vector, and thus lacks replicative potential and also avoids a host-to-virus immune response. The parent vector contains only the minimal cis-acting sequences necessary for transcription, reverse transcription, integration, and packaging of the lentiviral DNA in 7.8 kb genome. The lentivirus contained vesicular stomatitis virus (VSV-G) envelope, which has been shown to be superior for transducing mouse hematopoietic stem cells. The LeGO-iG2-sCD137 lentivirus vector was transduced into in two different eukaryote cell lines, NIH3T3 and HEK293 cells (see Example 1). The human embryonic kidney 293 (HEK293) cells were used for efficient transfection and higher protein expression and mouse fibroblast (NIH3T3) cells were used for necessary glycosylation and proper folding of the mouse protein. Stably transduced cell lines were sorted for high and medium EGFP expression and the sorted cells were grown for five days in IMDM complete media (FIG. 15*b*). The quantity of secreted soluble CD137 produced from these cells was determined by ELISA.

$0.5\times10^6$ NIH3T3 cells, either un-transfected (thin solid line), un-sorted (even dashed line), sorted on medium expression of EGFP (uneven dashed line), or sorted on high expression of EGFP (thick solid line) were identified using a four-laser FACSAria II. Recovered cells were cultured in IMDM for 3 weeks after the original sort and stable EGFP expression assessed by FACSCalibur. (c) Mouse NIH3T3 fibroblasts and human embryonic kidney (HEK293) cells were transduced with lentiviral particles LeGO-iG2-sCD137. The transduced NIH3T3 and HEK293 cells exhibiting stable EGFP expression were sorted for high (top 10%) and medium (middle 40-70%) EGFP expression using a FACS Arial II flow cytometry. The sorted cell lines were subsequently re-plated and cultured for an additional five days in IMDM with 10% FBS before checking soluble CD137 expression by ELISA.

The results show that HEK293-EGFP high expressers produced greater amounts of soluble CD137 protein compared to HEK293-EGFP medium expressers, non-sorted cells, or NIH3T3 transduced cells (FIG. 15*c*). Since HEK293-EGFP high expressers produced the highest amounts of soluble CD137, we used these cell lines for further purification and characterization of the soluble protein. The overall expression of EGFP in the sorted cell lines was determined by flow cytometry following three weeks in culture (data not shown). The lentivirally-produced soluble CD137 made in both mouse NIH3T3 and human HEK293 cell lines was similar in gel mobility and exhibited identical physical characteristics (multimeric size, sugar modification degree), indicating that the proteins produced from the two cell lines do not differ in post-translational modifications and are comparable to each other (data not shown).

Example 13

Soluble CD137 Exists Predominantly as a Dimer

Figure 16:
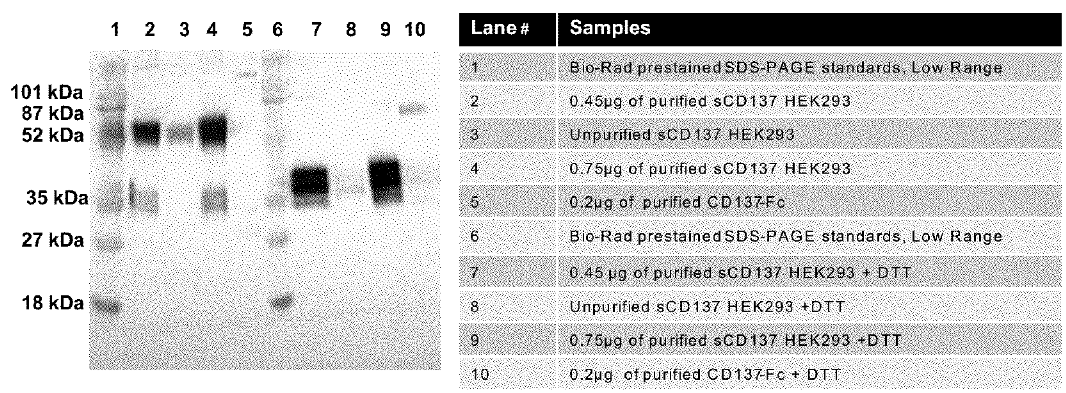
FIG. 16 shows that recombinant soluble CD137 protein, secreted from lentivirally-transduced HEK293 cells, exists primarily as dimers. (a) Western blot was performed on purified and unpurified soluble CD137 protein secreted into the media of transduced HEK293 cells and separated on a 12% Tris-Glycine SDS-page gel under non-reducing (−DTT, lanes 1-6) and reducing (+DTT, lanes 7-10) conditions. Purified soluble CD137 of different concentration (0.20 μg, 0.45 μg or 0.75 μg or an unknown amount) was loaded in each lane at 15 μL per lane. Low molecular weight protein standards serve as size markers (lanes 1 and 6). 0.2 μg of CD137-Fc fusion protein served as a control (lanes 5 and 10). (b) Analytical ultra-centrifugation (AUC) was performed on purified soluble CD137 from HEK293 cells. 1 OD of protein in PBS was used as the starting material. 500 μL of soluble CD137 was separated by AUC for 24 hours. The sCD137 multimers were characterized by sedimentation velocity and their molecular sizes estimated by curve fitting data analysis.
Figure 16:
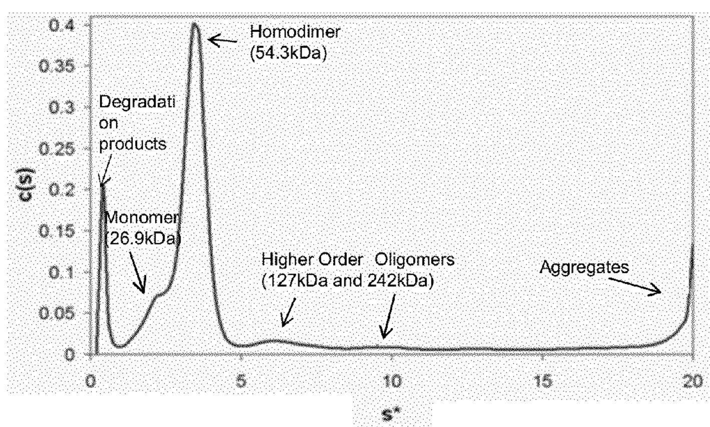

The size of soluble CD137 isolated from HEK293 high EGFP producer cells was assessed. Western blot was performed on purified and unpurified soluble CD137 protein secreted into the media of transduced HEK293 cells and separated on a 12% Tris-Glycine SDS-page gel under non-reducing (−DTT, lanes 1-6) and reducing (+DTT, lanes 7-10)

conditions (FIG. 16*a*). Purified soluble CD137 of different concentration (0.20 ug, 0.45 μg or 0.75 μg or an unknown amount) was loaded in each lane at 15 μL per lane. Low molecular weight protein standards serve as size markers (lanes 1 and 6). 0.2 μg of CD137-Fc fusion protein served as a control (lanes 5 and 10). Analytical ultra-centrifugation (AUC) was performed on purified soluble CD137 from HEK293 cells (FIG. 16*b*). 1 OD of protein in PBS was used as the starting material. 500 μL of soluble CD137 was separated by AUC for 24 hours. The sCD137 multimers were characterized by sedimentation velocity and their molecular sizes estimated by curve fitting data analysis.

The results show that unpurified soluble CD137 protein is mainly a ~55 kDa homodimer under non-reducing conditions and a ~35 kDa monomer under reducing conditions (FIG. 16*a*). These observations are consistent with previous reports, which show that soluble CD137 exists as both a 30 kDa monomer and a 55 kDa homodimer. Next, soluble CD137 was purified from the supernatant of HEK293 high-EGFP producer cells using affinity chromatography (see Example 1). Since ethylene glycol (EG) and magnesium chloride ($MgCl_2$) have shown to avoid the degradation or alteration of the target molecule during disassociation from the affinity column, these solvents were used during elution. After elution under non-reducing buffer conditions, western blot analysis was performed on quantified purified protein at two different doses (0.45 μg and 0.75 μg). The observed sizes of the purified protein were equivalent to previous observations with unpurified protein and again showed a homodimer at ~55 kDa and a monomer at ~35 kDa (FIG. 16*a*, lane 2 & 4), indicating that binding and elution from the affinity column did not affect the physical structure of the protein.

It is important to note that soluble CD137 exists predominantly as a dimer under non-reducing conditions, but as a monomer under reducing conditions, strongly suggesting that the dimer is linked by a disulfide bond (FIG. 16*a*, lane 2 & 4 vs. lane 7 & 9). This is in accord with sequence homology data indicating the existence of both parallel and anti-parallel homodimerization domains in the CD137 structure. Three distinct monomer bands were also seen on the reduced western blot, suggesting that the purified protein is differentially glycosylated (0, 1, or 2 glycosylation; FIG. 16*a*, lane 7 & 9). This is consistent with the predicted protein sequence indicating that soluble CD137 protein harbors two canonical N-linked glycosylation. To further confirm the structure of purified protein, we used analytical ultra-centrifugation (AUC), a gold standard for analyzing protein structure. This method showed that the bulk of soluble CD137 was present as a 54.3 kDa dimer, with a small amount of monomer sedimenting at 26.9 kDa (FIG. 16*b*). Surprisingly 12% of the total soluble CD137 formed higher order oligomers and/or aggregates at elevated concentrations (FIG. 16*b*); this suggests that soluble CD137 may possess more than one protein-protein association domain, which allows for different multimeric forms.

Example 14

Soluble CD137 Suppress Proliferation and Cell Cycle Progression of CD4 T Cells In Vitro Purified soluble CD137 was used to confirm suppression of CD4 T cells in vitro. CFSE-stained CD4 T cells with CD3/CD28 beads were cultured with or without soluble CD137.

Figure 17:
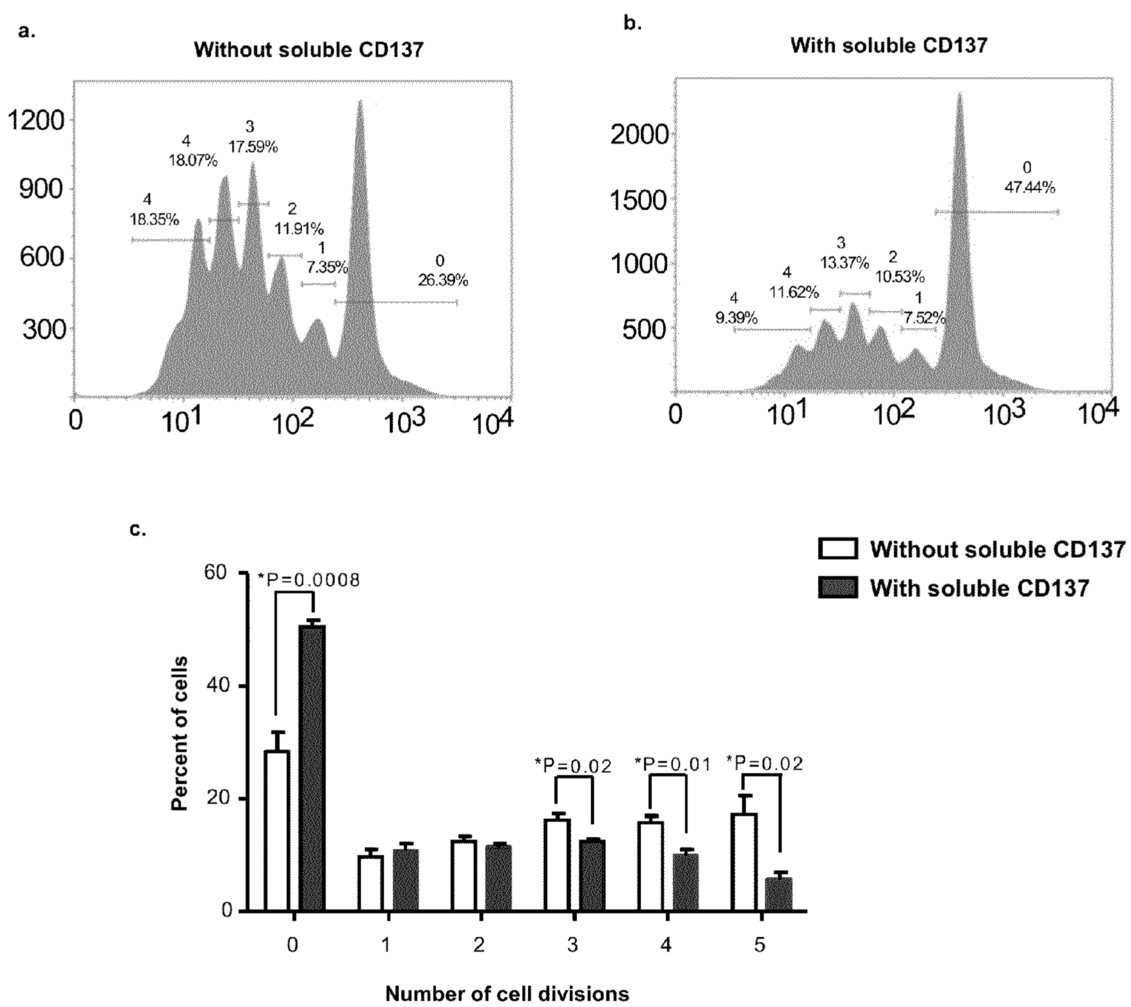
FIG. 17 shows that purified soluble CD137 suppresses CD4 T cell proliferation in vitro. (a, b) CD4 T cells were mini mac purified from 6-8 week old NOD mice and labeled with carboxyfluorescein succinimidyl ester (CFSE). $1\times10^5$ CD4 T cells, stimulated with 20,000 CD3/CD28 beads, were cultured in a U-bottom 96-well plate for 3 days with or without 15 g of soluble CD137. After three days in culture, the cells were harvested and stained with CD4. The amount of proliferation was assessed by CFSE FACS. The percent of cells within each cell subset was calculated and graphed as histograms (n=4). Statistical analysis was performed using the unpaired t test. (c) Further analysis of the each division revealed that there is a significant reduction in the percent of cells in the third, fourth and fifth cell division with the addition of soluble CD137.

CD4 T cells were mini mac purified from 6-8 week old NOD mice and labeled with carboxyfluorescein succinimidyl ester (CFSE). $1\times10^5$ CD4 T cells, stimulated with 20,000 CD3/CD28 beads, were cultured in a U-bottom 96-well plate for 3 days with or without 15 μg of soluble CD137. After three days in culture, the cells were harvested and stained with CD4. The amount of proliferation was assessed by CFSE FACS. One representative of four independent experiments is shown (FIG. 17*a, b*). As indicated in FIGS. 17*a-b*, the percent of cells within each cell subset was calculated and graphed as histograms (n=4). Statistical analysis was performed using the unpaired t-test.

The results showed that addition of soluble CD137 protein significantly reduced the CFSE dilution consistent with reduction in the cell cycle progression in vitro (FIG. 17*a, b*). Further analysis of the each division revealed that there is a significant reduction in the percent of cells in the third, fourth and fifth cell division with the addition of soluble CD137 (FIG. 17*c*). This proved that the purified protein is biologically active and functionally suppressive. Further, it was observed that the culture treated with soluble CD137 did not have increased cell death compared to untreated cells (data not shown). Thus, the data indicate that the purified soluble CD137 is functionally suppressive but not physiologically harmful to the cells at the concentration used.

Example 15

Soluble CD137 Reduces the Incidence of Diabetes in NOD Mice

Figure 18:
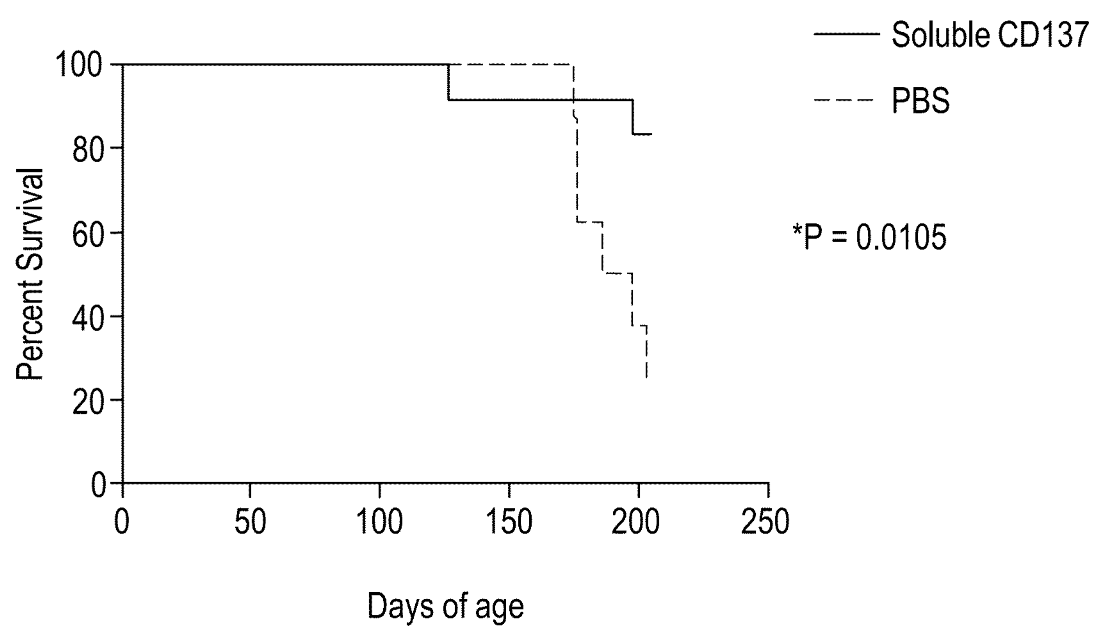
FIG. 18 shows that purified soluble CD137 prevents diabetes in vivo. Seven weeks old female NOD mice were treated with either PBS or with 20 ug of soluble CD137, once for four weeks (n=8 per group). The blood glucose level of the treated animals was tested for diabetes over time. The P value was calculated using the logrank statistic in Graphpad.

Seven week old female NOD mice were injected with 20 ug of purified soluble CD137 or PBS control, once every four weeks. The blood glucose level of the animals was tested for diabetes thereafter. The three PBS treated NOD mice showed the expected elevated blood glucose level over 600 mg/dL at 115 days (FIG. 18, dashed line). In contrast, the soluble CD137 treated NOD mice showed complete protection from diabetes up to 205 days (FIG. 18, solid line). These results showed that the recombinant soluble CD137 is functional in vivo and can prevent the onset of T1D in NOD mice.

All documents cited are incorporated herein by reference in their entirety; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of inhibiting progression of type 1 diabetes in a mammal comprising administering to the mammal a therapeutically effective amount of soluble CD137, thereby inhibiting progression of type 1 diabetes.

2. The method of claim 1, wherein the administering suppresses $CD4^{pos}$ non-regulatory T cells, thereby inhibiting progression of type 1 diabetes.

3. The method of claim 1, further comprising the steps of monitoring the mammal and repeating administration of said soluble CD137 one or more times, thereby inhibiting progression of type 1 diabetes.

4. The method of claim 1, wherein the mammal is a mouse or a human.

5. The method of claim 1, wherein said soluble CD137 is administered intravenously.

6. The method of claim 1, wherein said soluble CD137 is in the form of an injectable suspension.

* * * * *

SEQUENCE LISTING

```
<160> NUMBER OF SEQ ID NOS: 5

<210> SEQ ID NO 1
<211> LENGTH: 18
<212> TYPE: DNA
<213> ORGANISM: Mus musculus
```

-continued

```
<220> FEATURE:
<221> NAME/KEY: misc_feature
<223> OTHER INFORMATION: Forward primer, membrane bound CD137

<400> SEQUENCE: 1

cccccctgtgg tgagcttc                                                   18


<210> SEQ ID NO 2
<211> LENGTH: 18
<212> TYPE: DNA
<213> ORGANISM: Mus musculus
<220> FEATURE:
<221> NAME/KEY: misc_feature
<223> OTHER INFORMATION: Reverse primer, membrane bound CD137

<400> SEQUENCE: 2

aggagggcac tccttgca                                                   18


<210> SEQ ID NO 3
<211> LENGTH: 18
<212> TYPE: DNA
<213> ORGANISM: Mus musculus
<220> FEATURE:
<221> NAME/KEY: misc_feature
<223> OTHER INFORMATION: Forward primer, soluble CD137

<400> SEQUENCE: 3

cccccctgtgg tgagcttc                                                   18


<210> SEQ ID NO 4
<211> LENGTH: 23
<212> TYPE: DNA
<213> ORGANISM: Mus musculus
<220> FEATURE:
<221> NAME/KEY: misc_feature
<223> OTHER INFORMATION: Reverse primer, soluble CD137

<400> SEQUENCE: 4

gggaggacca gcatttaaga aga                                             23


<210> SEQ ID NO 5
<211> LENGTH: 16
<212> TYPE: DNA
<213> ORGANISM: Mus musculus
<220> FEATURE:
<221> NAME/KEY: misc_feature
<223> OTHER INFORMATION: Probe for membrane bound CD137 and soluble
      CD137 primer sets

<400> SEQUENCE: 5

tcccagtacc accatt                                                     16
```